United States Patent
Nativ et al.

(10) Patent No.: US 10,265,091 B2
(45) Date of Patent: Apr. 23, 2019

(54) SURGICAL STAPLER/CUTTER AND EXTENDED BUTTRESS

(71) Applicant: Ethicon, Inc., Somerville, NJ (US)

(72) Inventors: Nir I. Nativ, West Orange, NJ (US); Sridevi Dhanaraj, Somerville, NJ (US); Leo B. Kriksunov, Ithaca, NY (US); Charles J. Scheib, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 420 days.

(21) Appl. No.: 15/147,942

(22) Filed: May 6, 2016

(65) Prior Publication Data

US 2017/0303952 A1    Oct. 26, 2017

Related U.S. Application Data

(63) Continuation-in-part of application No. 15/133,407, filed on Apr. 20, 2016.

(51) Int. Cl.
| | | |
|---|---|---|
| A61B 17/32 | (2006.01) |
| A61B 17/068 | (2006.01) |
| A61B 17/10 | (2006.01) |
| A61B 17/072 | (2006.01) |
| A61B 17/00 | (2006.01) |

(52) U.S. Cl.
CPC ............ *A61B 17/32* (2013.01); *A61B 17/068* (2013.01); *A61B 17/07207* (2013.01); *A61B 17/07292* (2013.01); *A61B 17/105* (2013.01); *A61B 2017/00477* (2013.01); *A61B 2017/07271* (2013.01); *A61B 2017/07278* (2013.01); *A61B 2017/07285* (2013.01)

(58) Field of Classification Search
CPC ............ A61B 17/068; A61B 17/07207; A61B 17/07292; A61B 17/105; A61B 17/32
USPC .......................................... 227/175.1–180.1
See application file for complete search history.

(56) References Cited

U.S. PATENT DOCUMENTS

| | | |
|---|---|---|
| 4,805,823 A | 2/1989 | Rothfuss |
| 5,275,323 A | 1/1994 | Schulze et al. |
| 5,415,334 A | 5/1995 | Williamson, IV et al. |
| 5,465,895 A | 11/1995 | Knodel et al. |
| 5,597,107 A | 1/1997 | Knodel et al. |
| 5,632,432 A | 5/1997 | Schulze et al. |
| 5,673,840 A | 10/1997 | Schulze et al. |
| 5,704,534 A | 1/1998 | Huitema et al. |
| 5,814,055 A | 9/1998 | Knodel et al. |

(Continued)

*Primary Examiner* — Nathaniel C Chukwurah
(74) *Attorney, Agent, or Firm* — David R. Crichton; Leo B. Kriksunov

(57) ABSTRACT

The present invention is directed to surgical staplers stapling and resecting tissue comprising a surgical buttress at least partially disposed on a tissue facing surface of at least one of the cartridge or the anvil, said buttress having width substantially larger than width of said tissue facing surfaces; said buttress comprising a first portion positioned over the deployable staples or over the staple forming pockets, and at least one flap portion not positioned over the deployable staples or over the staple forming pockets; said flap portion folded or rolled on itself and configured to be unfurlable and wrappable about the resected tissue. The present invention is also directed to methods of use of such stapler assembly devices.

19 Claims, 32 Drawing Sheets

(56) References Cited

U.S. PATENT DOCUMENTS

| | | | |
|---|---|---|---|
| 6,325,810 B1 * | 12/2001 | Hamilton | A61B 17/07207 227/175.1 |
| 6,458,147 B1 | 10/2002 | Cruise | |
| 6,978,921 B2 | 12/2005 | Shelton, IV et al. | |
| 7,000,818 B2 | 6/2006 | Shelton, IV et al. | |
| 7,143,923 B2 | 12/2006 | Shelton, IV et al. | |
| 7,303,108 B2 | 12/2007 | Shelton, IV | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,721,930 B2 | 5/2010 | McKenna et al. | |
| 8,308,042 B2 | 11/2012 | Aranyi et al. | |
| 8,408,439 B2 | 4/2013 | Huang et al. | |
| 8,453,914 B2 | 6/2013 | Laurent et al. | |
| 8,657,176 B2 | 2/2014 | Shelton, IV et al. | |
| 8,746,535 B2 | 6/2014 | Shelton, IV et al. | |
| 8,864,009 B2 | 10/2014 | Shelton, IV et al. | |
| 9,113,865 B2 | 8/2015 | Shelton, IV et al. | |
| 9,113,873 B2 | 8/2015 | Marczyk et al. | |
| 9,168,038 B2 | 10/2015 | Shelton, IV et al. | |
| 9,186,142 B2 | 11/2015 | Fanelli et al. | |
| 9,198,662 B2 | 12/2015 | Barton et al. | |
| 9,220,501 B2 | 12/2015 | Baxter, III et al. | |
| 9,241,714 B2 | 1/2016 | Timm et al. | |
| 2006/0062768 A1 | 3/2006 | Hnojewyj | |
| 2011/0104280 A1 | 5/2011 | Hnojewyj | |
| 2013/0062391 A1 | 3/2013 | Boudreaux et al. | |
| 2014/0166721 A1 * | 6/2014 | Stevenson | A61B 17/068 227/176.1 |
| 2014/0239047 A1 | 8/2014 | Hodgkinson et al. | |
| 2014/0369991 A1 | 12/2014 | Schutte et al. | |
| 2015/0374373 A1 | 12/2015 | Rector et al. | |

* cited by examiner

Fig. 43
Fig. 43A
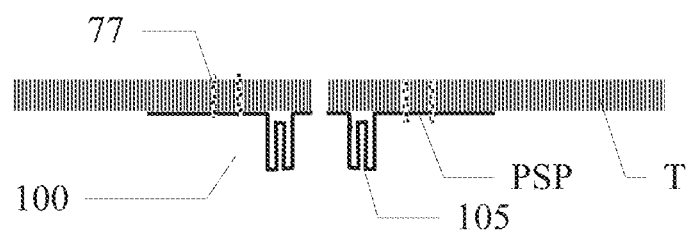
Fig. 43B
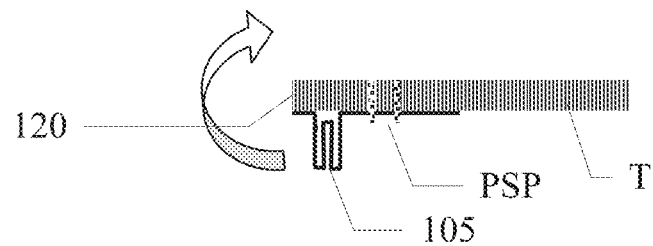
Fig. 43C
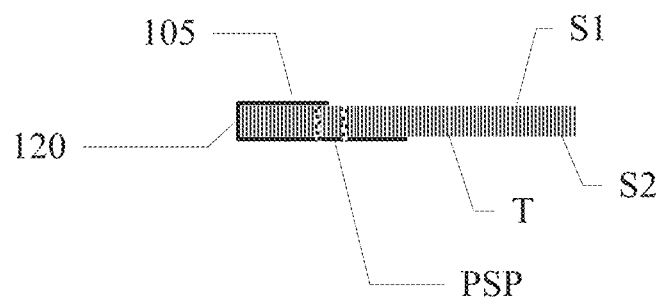

SURGICAL STAPLER/CUTTER AND EXTENDED BUTTRESS

FIELD OF THE INVENTION

The present invention relates to surgical instruments and methods for enhancing properties of tissue repaired or joined by surgical staples and, more particularly to surgical instruments and methods designed to apply a buttress material to enhance the properties of repaired or adjoined tissue at a target surgical site.

BACKGROUND OF THE INVENTION

Throughout the years the medical field has utilized various techniques in an effort to join or bond body tissue together. Historically, suturing was the accepted technique for rejoining severed tissues and closing wounds. Suturing is achieved with a surgical needle and a suturing thread, with the intended function of sutures to hold the edges of a wound or tissue against one another during the healing process. Staples are used to replace suturing when joining or anastomosing various body structures, such as, for example, the bowel. The surgical stapling devices employed to apply staples are generally designed to simultaneously cut and seal an extended segment of tissue in a patient.

Linear or annular surgical stapling devices are employed by surgeons to sequentially or simultaneously apply one or more rows of surgical fasteners, e.g., staples, to body tissue for the purpose of joining segments of body tissue together and/or for the creation of an anastomosis. Linear surgical stapling devices generally include a pair of jaws or finger-like structures between which body tissue to be joined is placed. When the surgical stapling device is actuated, firing bars move longitudinally and contact staple drive members in one of the jaws, and surgical staples are pushed through the body tissue and into and against an anvil in the opposite jaw thereby crimping the staples closed. A knife blade may be provided to cut between the rows/lines of staples.

A number of surgical staplers for use in open and endoscopic procedures are known. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents is incorporated by reference herein.

While many of the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to cut and close a vessel leading to a lung. For instance, the vessels leading to an organ may be severed and closed by a stapler before removal of the organ from the thoracic cavity. Surgical staplers may be used in various other settings and procedures. Examples of surgical staplers that may be particularly suited or use through a thoracotomy are disclosed in U.S. Pat. No. 9,186,142, entitled "Surgical Instrument End Effector Articulation Drive with Pinion and Opposing Racks", the disclosure of which is incorporated by reference herein.

A number of buttresses and tissue thickness compensators which are disposed on tissue and stapled to said tissue are known in the art. A reference is made to U.S. Pat. No. 8,657,176 Tissue thickness compensator for a surgical stapler; U.S. Pat. No. 8,746,535 Tissue thickness compensator comprising detachable portions; U.S. Pat. No. 8,864,009 Tissue thickness compensator for a surgical stapler comprising an adjustable anvil; U.S. Pat. No. 9,113,865 Staple cartridge comprising a layer; U.S. Pat. No. 9,168,038 Staple cartridge comprising a tissue thickness compensator; U.S. Pat. No. 9,198,662 Tissue thickness compensator having improved visibility; U.S. Pat. No. 9,220,501 Tissue thickness compensators; U.S. Pat. No. 9,241,714 Tissue thickness compensator and method for making the same; U.S. Pat. No. 8,308,042 Structure for attachment of buttress material to anvils and cartridges of surgical stapler; U.S. Pat. No. 9,113,873 Detachable buttress material retention systems for use with a surgical stapling device.

U.S. Patent publication No. 2014/0239047 ADHERENCE CONCEPTS FOR NON-WOVEN ABSORBABLE FELT BUTTRESSES discloses a surgical stapling apparatus, comprising: a housing; a handle supported by the housing; an elongated body extending distally from the housing; a tool assembly at the distal end of the elongated body, the tool assembly including: a cartridge assembly including a staple cartridge having a tissue facing surface, a plurality of staple retaining pockets and a knife slot formed in the tissue facing surface thereof; a plurality of surgical fasteners loaded one each in the staple retaining pockets; and an anvil assembly in juxtaposed relation to the cartridge assembly, the anvil assembly including an anvil plate having a tissue facing surface defining a plurality of staple forming pockets and a knife slot therein, at least one of the cartridge assembly or the anvil assembly being movable in relation to the other of the cartridge assembly and the anvil assembly; and a surgical buttress attached to the tissue facing surface of at least one of the cartridge assembly or the anvil assembly, the surgical buttress conforming to the tissue facing surface such that the surgical buttress is deformed locally into the staple retaining pockets and the knife slot of the cartridge assembly or the staple forming pockets and the knife slot of the anvil assembly to which the surgical buttress is attached, thereby increasing the contact area between the surgical buttress and the tissue facing surface.

U.S. Patent publication No. 2013/0062391 SURGICAL INSTRUMENT WITH FLUID FILLABLE BUTTRESS discloses an apparatus, comprising: (a) a surgical cutter comprising a distal end and a proximal end, wherein the proximal end comprises a handle, wherein the distal end comprises an anvil and a lower jaw, wherein the anvil and the lower jaw are configured to clamp tissue, wherein the surgical cutter is configured to sever tissue clamped by the anvil and the lower jaw; and (b) a buttress filled with a liquid, wherein the buttress is configured to be placed between the anvil and the lower jaw, wherein the buttress comprises a compressive portion and a pressure portion, wherein the compressive portion is configured to be squeezed by the distal end of the surgical cutter by the anvil and the lower jaw clamping the compressive portion, wherein the pressure portion is configured to be pressurized with the liquid in response to clamping on the compression portion, wherein the buttress is configured to be severed and stapled by the surgical cutter substantially contemporaneously with when the surgical cutter severs tissue, wherein the pressure portion is configured to urge the liquid through the compressive portion once the buttress is severed.

U.S. Pat. No. 6,325,810 FOAM BUTTRESS FOR STAPLING APPARATUS discloses apparatus for hemostasis or pneumostasis of tissue comprising a staple cartridge containing a plurality of surgical staples provided in two spaced apart lines having an upper surface with an opening through which said staples may be ejected, said upper surface having releasably attached thereto a compliant bioabsorbable open cell foam, wherein the open cell foam has at least one surface that has been substantially sealed that is in contact with the upper surface of the cartridge.

Post-operative leakage and delayed healing of the stapled tissue seals, particularly the edges of resected and stapled tissue may lead to morbidity and mortality. The existing staplers, even when pre-loaded with a buttress leave the resected tissue edge exposed resulting in potential blood and or body fluids leakage, infection, and adhesions. There is a need in improving the healing of the resected and stapled tissue to improve the viability of the tissue joined by staples.

SUMMARY OF THE INVENTION

The present invention relates to surgical instruments and methods for enhancing properties of tissue repaired or joined by surgical staples and, more particularly to surgical instruments and methods designed to apply a therapeutic material to enhance the properties of repaired or adjoined tissue at a target surgical site.

The present invention, in one embodiment, relates to a surgical stapler for joining and resecting tissue comprising: a body, a shaft assembly, and an end effector, wherein the end effector comprises a lower jaw configured to receive a staple cartridge, an anvil pivotable toward and away from the lower jaw, and a translatable knife member; a disposable cartridge installed in the lower jaw, said cartridge containing a plurality of deployable staples in arrays separated by a tissue resection channel through which the knife member can translate; said anvil having a plurality of staple forming pockets aligned with said deployable staples; a surgical buttress at least partially disposed on a tissue facing surface of at least one of the cartridge or the anvil, said buttress having width substantially larger than width of said tissue facing surfaces; said buttress comprising a first portion positioned over the deployable staples or over the staple forming pockets, and at least one flap portion not positioned over the deployable staples or over the staple forming pockets; said flap portion folded or rolled on itself and configured to be unfurlable and wrappable about the resected tissue.

The present invention, in another embodiment, relates to methods of joining tissue using the surgical stapler, comprising the steps of: inserting the staple cartridge into the lower jaw; capturing tissue between the anvil and the staple cartridge; translating the knife member distally from a proximal position to a distal position; substantially simultaneously cutting the captured tissue forming a resected tissue edge and driving the plurality of staples of the staple cartridge through the captured tissue, substantially simultaneously attaching said first portion of said buttress to a first tissue surface with staples and cutting said buttress in two halves while not attaching said flap portions to said tissue with said staples; removing said surgical stapler from contact with tissue leaving said buttress attached to the first tissue surface; unfurling at least one of said flap portions and wrapping said at least one flap portion around the resected tissue edge and optionally bringing said at least one flap portion in contact with a second tissue surface opposing the first tissue surface.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIGS. 43A-C show a schematic cross-sectional views of tissue and buttress having central flaps after stapling and removal of the surgical stapler, illustrating unfurling and wrapping flaps around resected surface and opposing tissue surface;

DETAILED DESCRIPTION OF THE INVENTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Surgery often involves joining of two or more layers of tissue together with optional simultaneous sectioning of a portion of the tissue along the staple line. Typical surgical stapling instruments, such as surgical linear stapling instruments have a staple-containing component and an opposing anvil component, between which at least two tissue layers to be joined are compressed prior to delivery of staples from the staple-containing component, whereby staples are piercing both tissue layers and are bent, deformed, or closed against the opposing anvil component. For linear surgical staplers, a disposable stapling cartridge is the staple-containing component, the cartridge typically installed in a jaw of the device, such as in a lower jaw adapted to hold the cartridge, and the opposing or upper jaw is the anvil component. The cartridge has a slot disposed between adjacent, parallel rows of staples and extending substantially the entire length of the rows of staples. The stapler includes firing means for the staples and a cutting means that is movable along the slot.

Referring now to FIGS. 1-6, a surgical stapling instrument or stapler is shown, with the figures taken from the U.S. Patent Publication No. 2015/0374373A1 "METHOD OF USING LOCKOUT FEATURES FOR SURGICAL STAPLER CARTRIDGE" which is incorporated by reference herein in its entirety.

Figure 1:
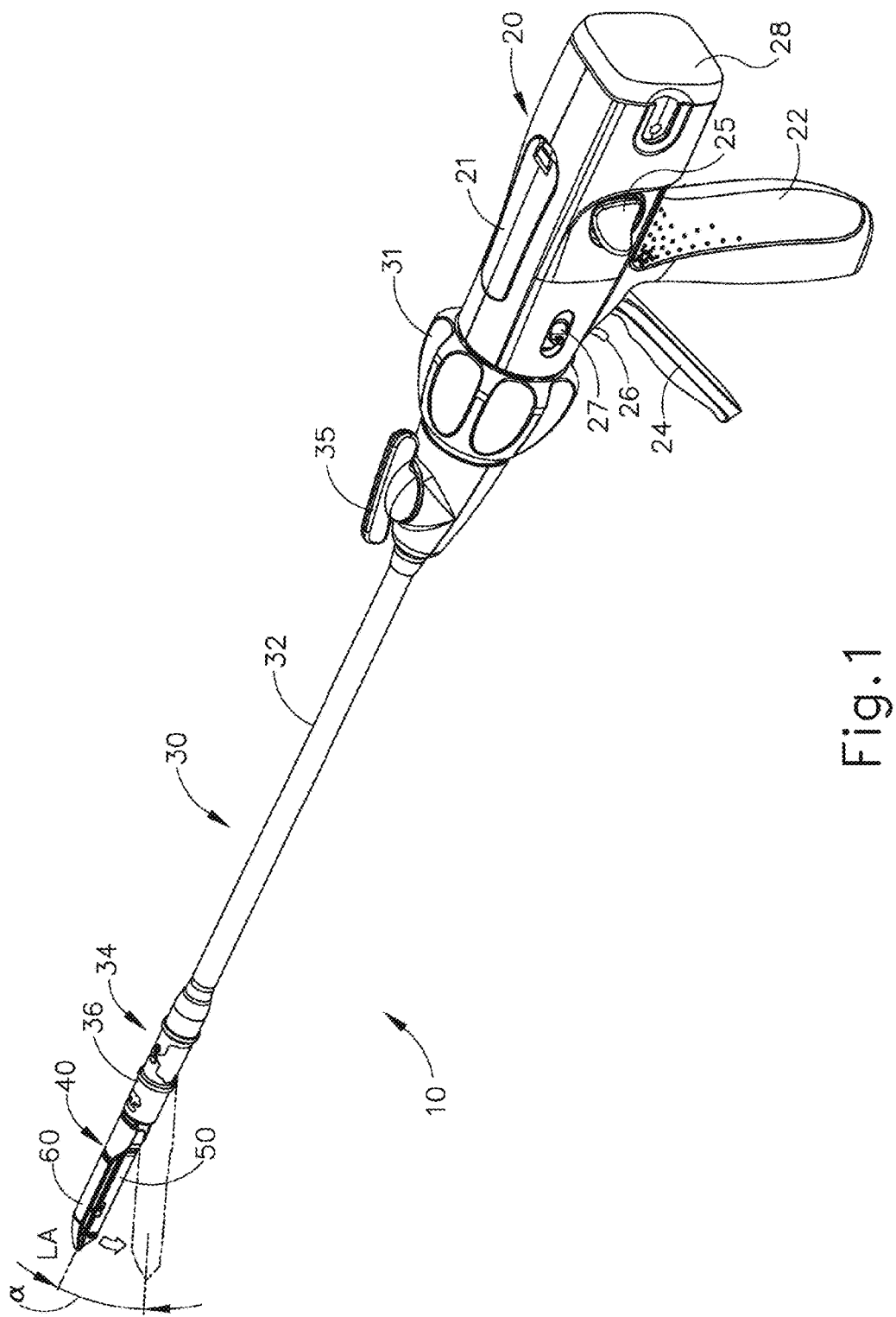
FIG. 1 depicts a perspective view of an exemplary articulating surgical stapling instrument.

FIG. 1 depicts an exemplary surgical stapling and cutting instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

Figure 2:
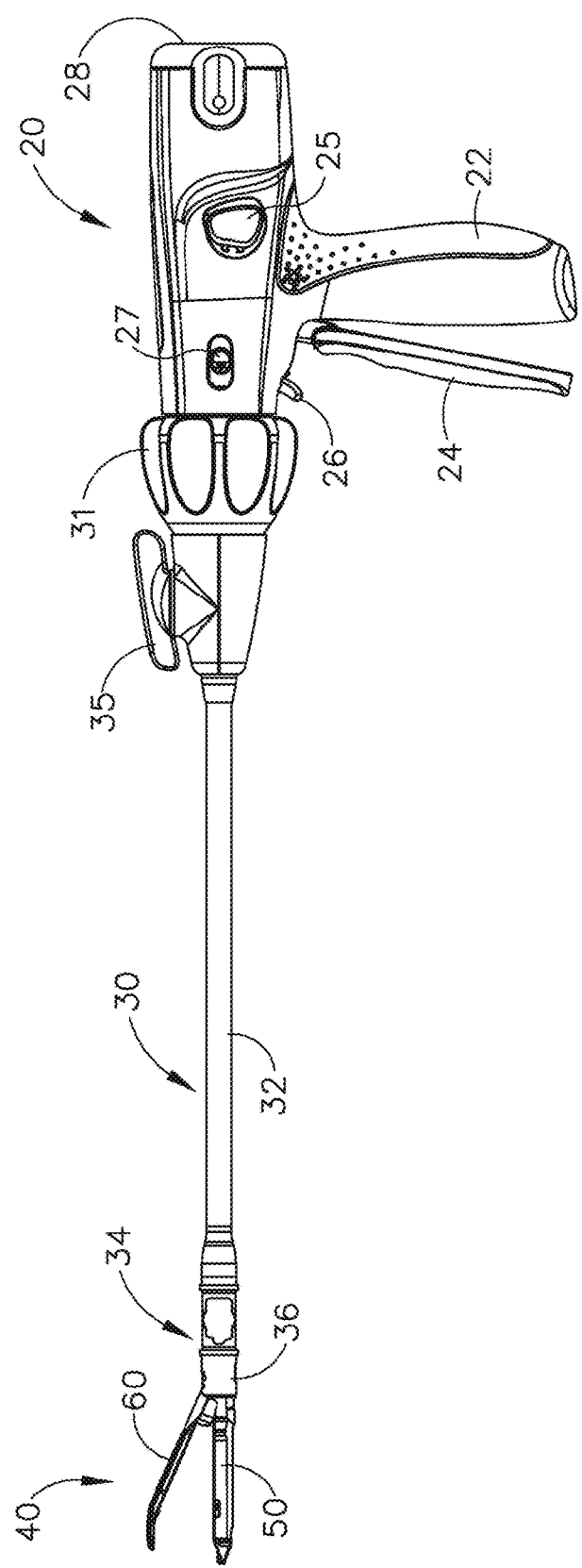
FIG. 2 depicts a side elevational view of the instrument of FIG. 1.

As shown in FIGS. 1-2, handle assembly (20) of the present example comprises pistol grip (22), a closure trigger (24), and a firing trigger (26). Each trigger (24, 26) is selectively pivotable toward and away from pistol grip (22). Handle assembly (20) further includes an anvil release button (25), a firing beam reverse switch (27), and a removable battery pack (28). Handle assembly (20) may have a variety of other components, features, and operabilities, in addition to or in lieu of any of those noted above.

Figure 3:
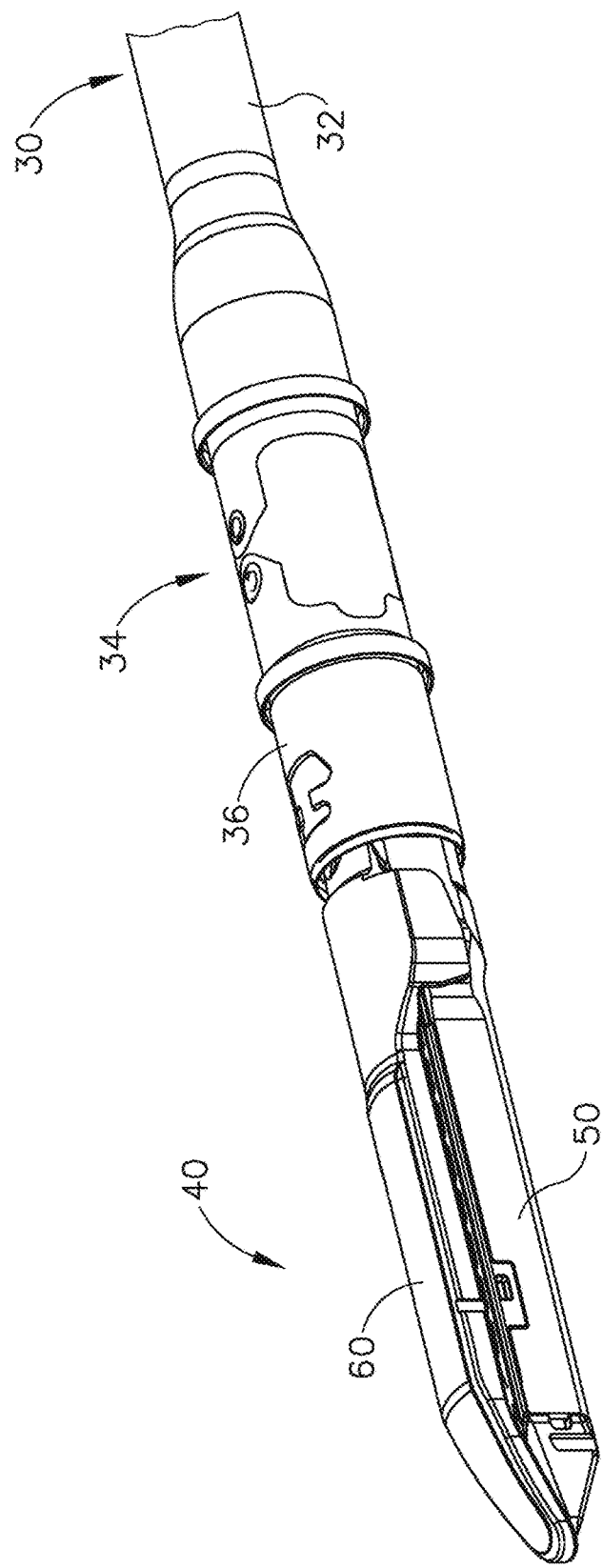
FIG. 3 depicts a perspective view of an end effector of the instrument of FIG. 1, with the end effector in a closed configuration.

As shown in FIGS. 1-3, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34).

Articulation section (34) is operable to laterally deflect closure ring (36) and end effector (40) laterally away from the longitudinal axis (LA) of shaft assembly (30) at a desired angle (a). End effector (40) may thereby reach behind an organ or approach tissue from a desired angle or for other reasons. In some versions, articulation section (34) enables deflection of end effector (40) along a single plane. In some other versions, articulation section (34) enables deflection of end effector along more than one plane. In the present example, articulation is controlled through an articulation control knob (35) which is located at the proximal end of shaft assembly (30). Knob (35) is rotatable about an axis that is perpendicular to the longitudinal axis (LA) of shaft assembly (30). Closure ring (36) and end effector (40) pivot about an axis that is perpendicular to the longitudinal axis (LA) of shaft assembly (30) in response to rotation of knob (35). By way of example only, rotation of knob (35) clockwise may cause corresponding clockwise pivoting of closure ring (36) and end effector (40) at articulation section (34). Articulation section (34) is configured to communicate longitudinal translation of closure tube (32) to closure ring (36), regardless of whether articulation section (34) is in a straight configuration or an articulated configuration.

As shown in FIGS. 1-2, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). In some versions, rotation knob (31) is operable to selectively lock the angular position of shaft assembly (30) and end effector (40) relative to handle assembly (20) about the longitudinal axis (LA) of shaft assembly (30). For instance, rotation knob (31) may be translatable between a first longitudinal position, in which shaft assembly (30) and end effector (40) are rotatable relative to handle assembly (20) about the longitudinal axis (LA) of shaft assembly (30); and a second longitudinal position, in which shaft assembly (30) and end effector (40) are not rotatable relative to handle assembly (20) about the longitudinal axis (LA) of shaft assembly (30). Of course, shaft assembly (30) may have a variety of other components, features, and operabilities, in addition to or in lieu of any of those noted above.

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Pins (66) and slots (54) are shown in FIG. 5. Anvil (60) is pivotable toward and away from lower jaw (50) between an open position (shown in FIGS. 2 and 4) and a closed position (shown in FIGS. 1, 3). As seen in FIG. 5, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40).

As seen in FIGS. 4-7, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (77) is positioned in each staple pocket (74). A staple driver (75) is also positioned in each staple pocket (74), underneath a corresponding staple (77), and above tray (76). Staple drivers (75) are operable to translate upwardly in staple pockets (74) to thereby drive staples (77) upwardly through staple pockets (74) and into engagement with anvil (60). Staple drivers (75) are driven upwardly by a wedge sled (78), which is captured between cartridge body (71) and tray (76), and which translates longitudinally through cartridge body (71). Wedge sled (78) includes a pair of obliquely angled cam surfaces (79), which are configured to engage staple drivers (75) and thereby drive staple drivers (75) upwardly as wedge sled (78) translates longitudinally through cartridge (70).

It should be understood that the configuration of staple cartridge (70) may be varied in numerous ways. For instance, staple cartridge (70) of the present example includes two longitudinally extending rows of staple pockets (74) on one side of channel (72); and another set of two longitudinally extending rows of staple pockets (74) on the other side of channel (72). However, in some other versions, staple cartridge (70) includes three, one, or some other number of staple pockets (74) on each side of channel (72).

Figure 4:
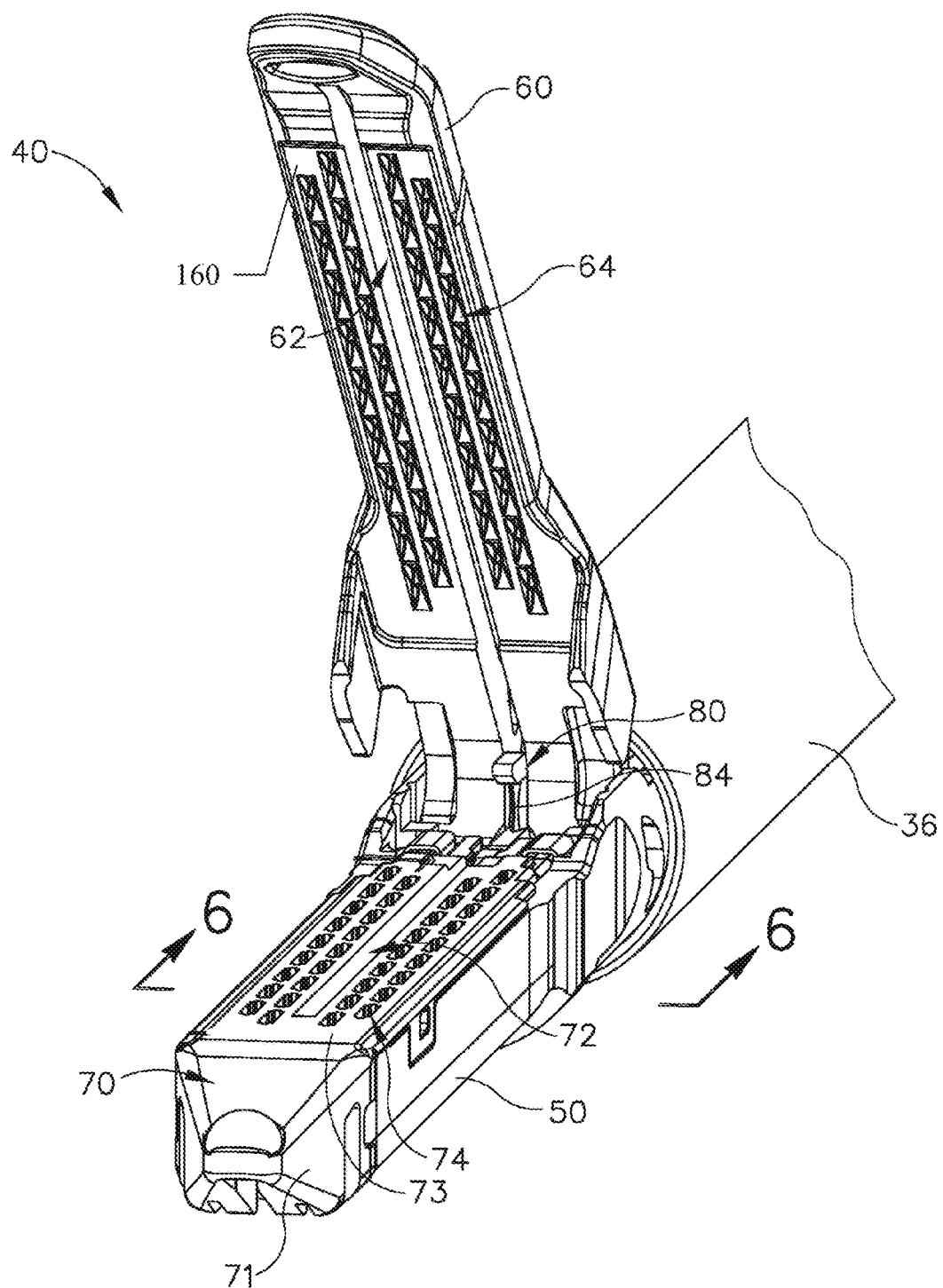
FIG. 4 depicts a perspective view of the end effector of FIG. 3, with the end effector in an open configuration.
Figure 5:
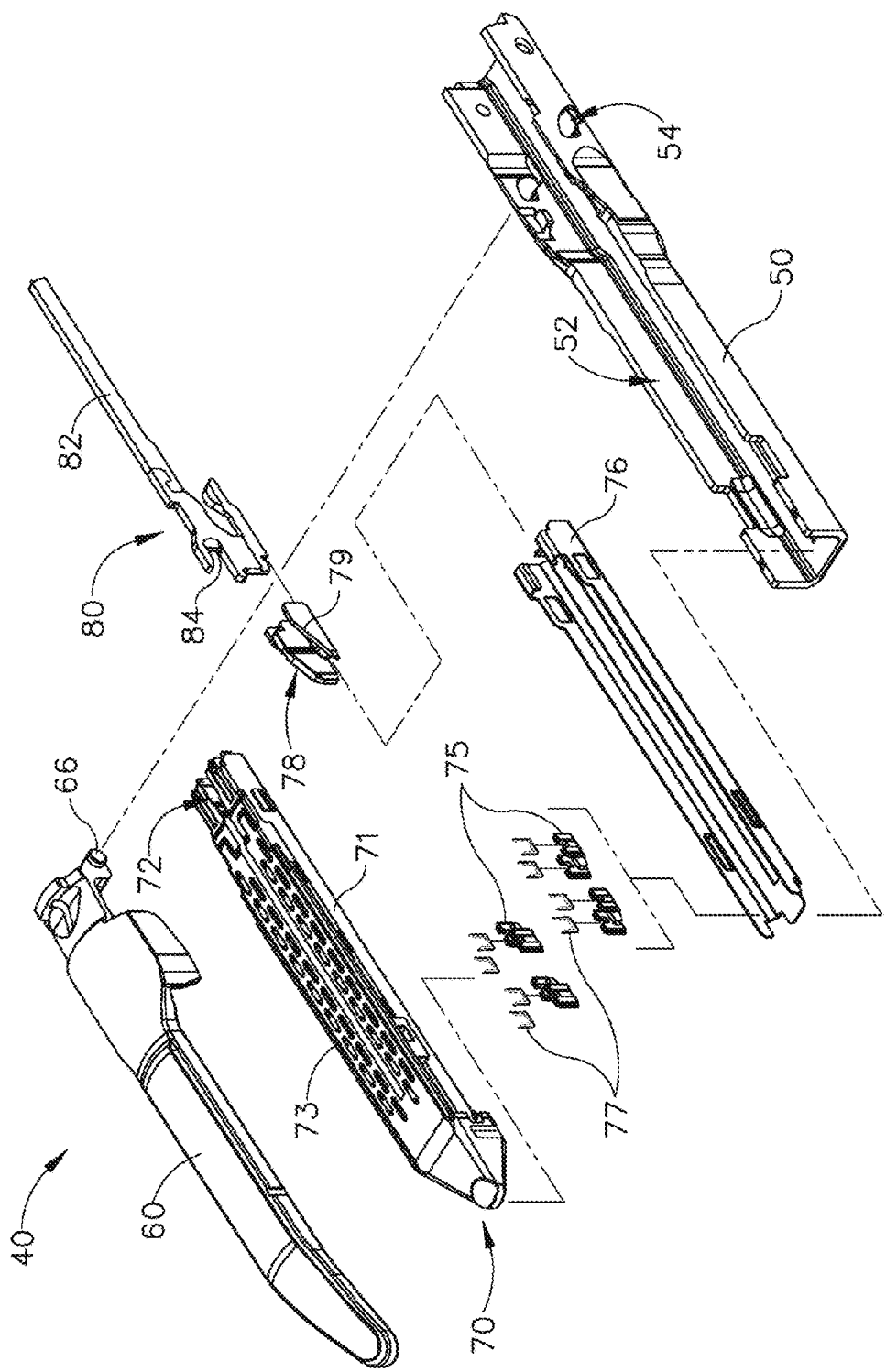
FIG. 5 depicts an exploded perspective view of the end effector of FIG. 3.

As seen in FIG. 4, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (77) when staples (77) are driven through tissue and into anvil (60). In particular, staple forming pockets (64) are configured to bend the legs of staples (77) to secure the formed staples (77) in the tissue.

Figure 6:
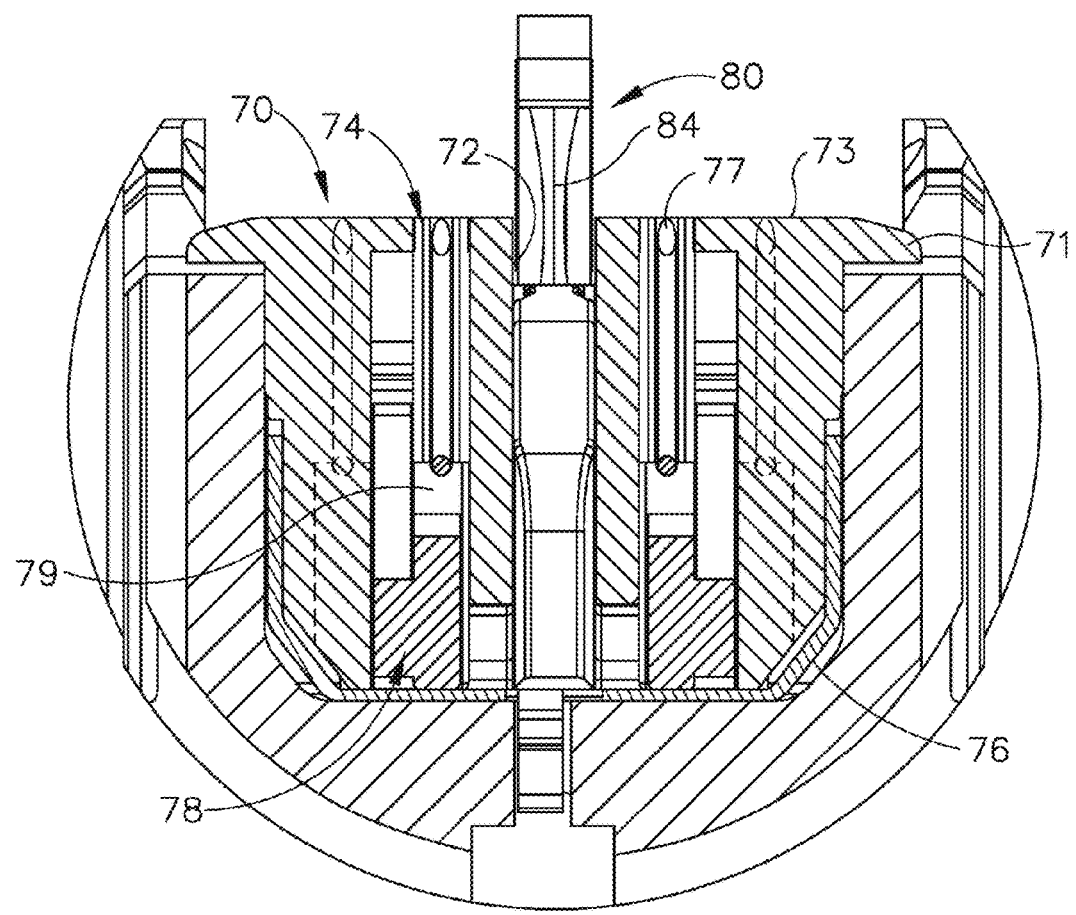
FIG. 6 depicts a cross-sectional end view of the end effector of FIG. 3, taken along line 6-6 of FIG. 4.
Figure 7:
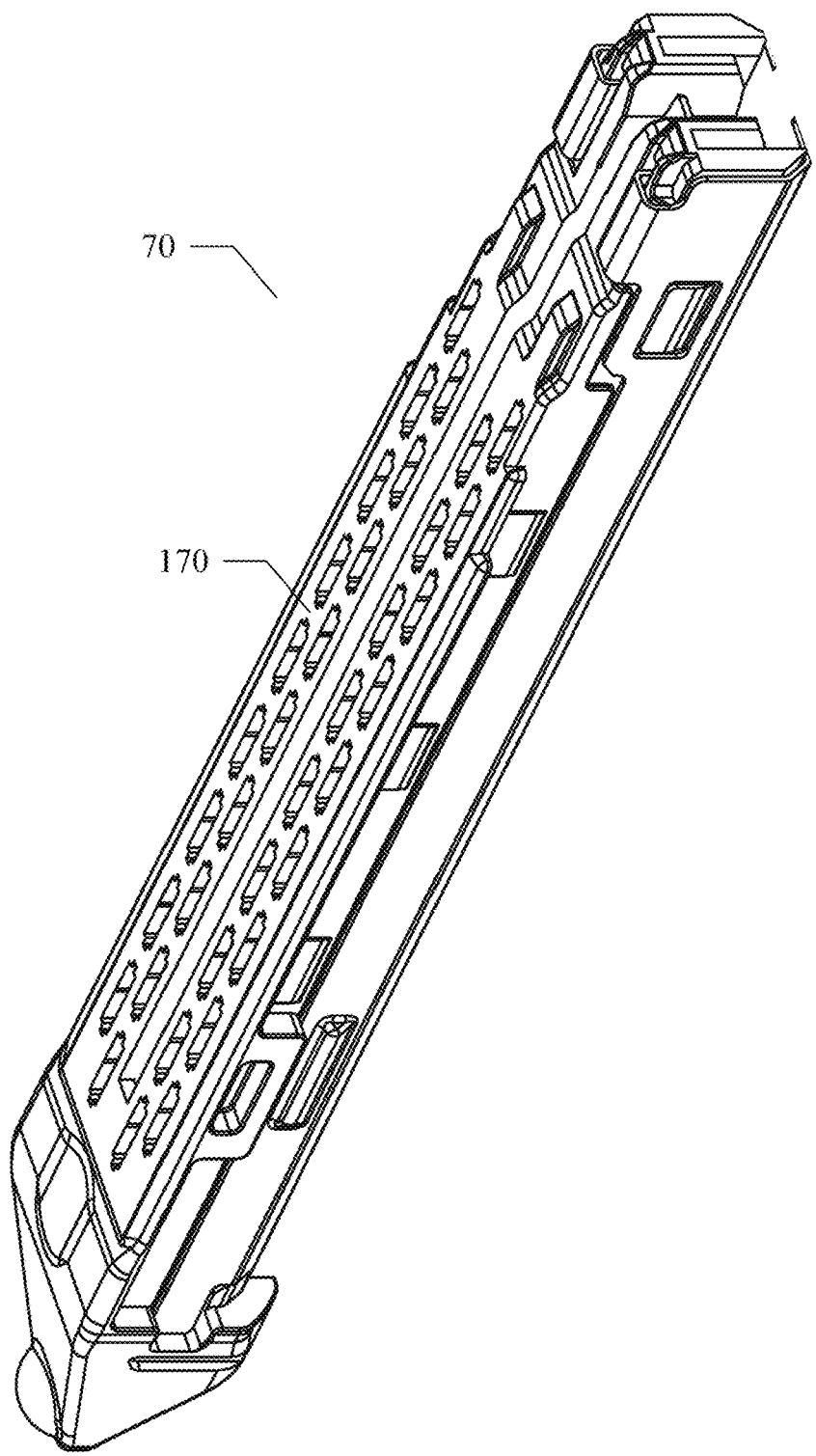
FIG. 7 depicts a perspective view of an exemplary cartridge that may be incorporated into the end effector of FIG. 3.

In the present example, a knife member (80) is configured to translate through end effector (40). As seen in FIG. 5, knife member (80) is secured to the distal end of a firing beam (82). As seen in FIGS. 4 and 6, knife member (80) is positioned in channels (62, 72) of anvil (60) and staple cartridge (70). Knife member (80) includes a distally presented cutting edge (84) that is configured to cut tissue that is compressed between anvil (60) and deck (73) of staple cartridge (70) as knife member (80) translates distally through end effector (40).

In some versions, end effector (40) includes lockout features that are configured to prevent knife member (80) from advancing distally through end effector (40) when a staple cartridge (70) is not inserted in lower jaw (50). In addition or in the alternative, end effector (40) may include lockout features that are configured to prevent knife member (80) from advancing distally through end effector (40) when a staple cartridge (70) that has already been actuated once (e.g., with all staples (77) deployed therefrom) is inserted in lower jaw (50). Alternatively, end effector (40) may simply omit such lockout features.

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40).

As noted above, handle assembly (20) includes a pistol grip (22) and a closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein. When closure trigger (24) reaches a fully pivoted state, such that anvil (60) is in a fully closed position relative to lower jaw (50), locking features in handle assembly (20) lock the position of trigger (24) and closure tube (32), thereby locking anvil (60) in a fully closed position relative to lower jaw (50). These locking features are released by actuation of anvil release button (25). Anvil release button (25) is configured and positioned to be actuated by the thumb of the operator hand that grasps pistol grip (22). In other words, the operator may grasp pistol grip (22) with one hand, actuate closure trigger (24) with one or more fingers of the same hand, and then actuate anvil release button (25) with the thumb of the same hand, without ever needing to release the grasp of pistol grip (22) with the same hand. Other suitable features may be used to actuate anvil (60).

Figure 8:
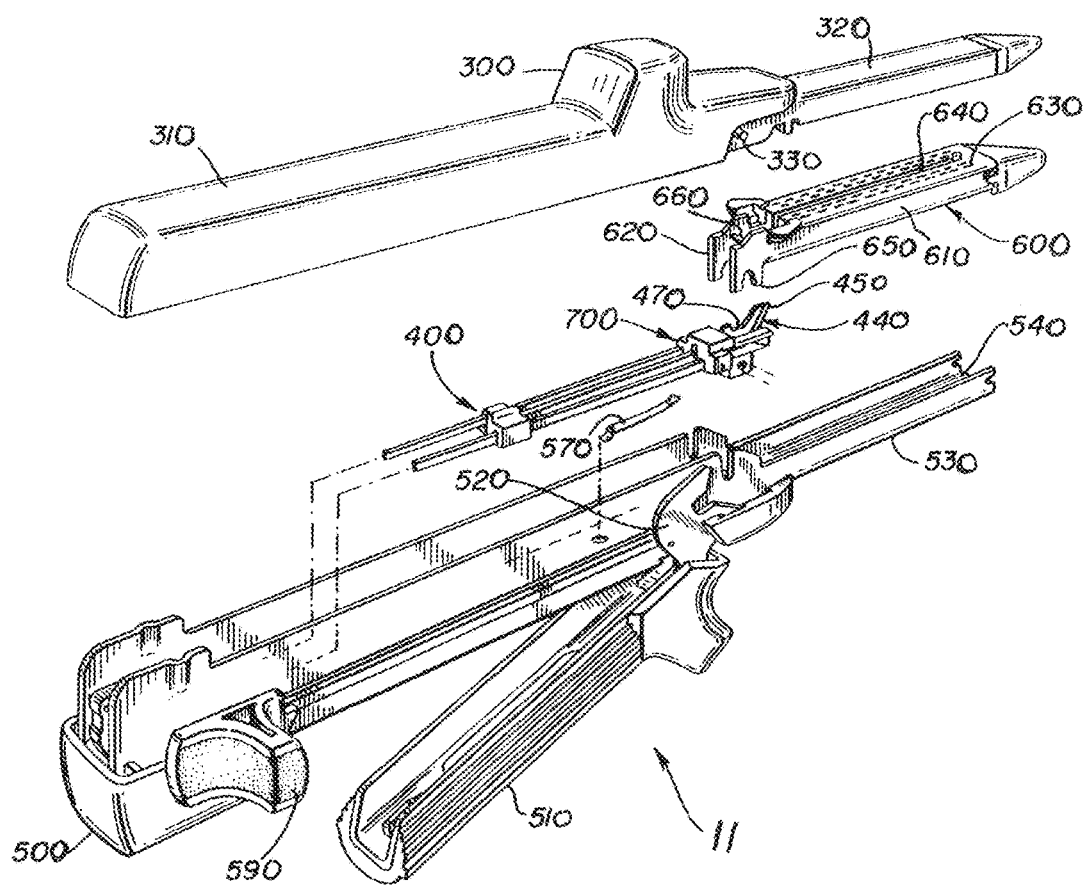
FIG. 8 shows an exploded perspective view of an alternative exemplary surgical stapling instrument.

Referring now to FIG. 8, an alternative exemplary surgical stapling instrument or linear stapler device is shown, with the figure adapted from the U.S. Pat. No. 5,275,323 "Surgical stapler" and incorporated by reference herein in its entirety. As seen in FIG. 8, surgical stapler 11 comprises an upper piece 300, a firing means 400, a lower piece 500 and a staple cartridge 600.

Staple cartridge 600 fits within the lower piece 500. Specifically, the front part of staple cartridge 600 fits into lower jaw channel 540. More specifically, the parallel side walls 610 of the staple cartridge 600 fit within the lower jaw channel 540. The back part of staple cartridge 600 has a breakable transverse member 660. This breakable transverse member 660 is placed on top of cartridge locking means 470 of firing means 400. At the same time two legs 650 within rearwardly extending surfaces 620 secure staple cartridge 600 to lower piece 500.

In FIG. 8, upper piece 300 has a rear upper handle portion 310 and a front upper jaw portion or anvil 320. Likewise, lower piece 500 includes a rear movable lower handle portion 510 and a front lower jaw portion 530. The embodiment of the surgical stapler as illustrated in FIG. 8 incorporates firing means 400, leaf spring 570, and staple cartridge 600 into lower piece 500. Yet, these elements may be placed in upper piece 300 instead of lower piece 500.

Lower handle portion 510 illustrated in FIG. 8 is movable, more specifically, pivotable between two locking positions. In the first locking position, movable lower handle portion 510 is positioned at an oblique angle to lower jaw portion 530. During the first locking position a C-shaped member 520 of lower handle 510 is disengaged from a stationary locking pin 330. The upper and lower pieces, 300 and 500, respectively may be separated before or after operation of stapler 11 in the first locking position. On the other hand, in the second locking position the C-shaped member 520 of movable lower handle 510 locks the upper and lower pieces 300 and 500 together. In the second locking position the movable lower handle portion 510 is parallel to lower jaw portion 520. This second locking position occurs by engaging stationary locking pin 330 with C-shaped member 520. This movable handle portion design may be on the upper or lower handle portions, 310 and 510, respectively.

Firing knob 590 activates firing means 400. Firing means 400 also includes a roof assembly 700 and also contains a cutting means such as a knife blade assembly 440. A cutting surface 450 is included in knife blade assembly 440. Although a knife blade assembly is illustrated in FIG. 8, tissue may be cut in many ways besides knife or razor blade cutting.

When knife blade assembly 440 is in alignment with slot 640, firing knob 590 is manually pushed towards staple cartridge 600. Pushing firing knob 590 moves knife blade assembly 440 forward toward the staple cartridge 600. Then knife cutting surface 450 is moved through slot 640 of staple cartridge 600 simultaneously advancing staples from staple cartridge 600 through longitudinal slots 630. In some staple cartridge 600 embodiments, knife blade assembly is incorporated into the staple cartridge 600.

Other versions and modifications of the surgical staplers 10, 11 are known to a skilled artisan, all including a staple cartridge 70 or 600 having a plurality of staple pockets 74 or longitudinal slots 630 containing staples 77 (staples are not shown in FIG. 8), with staple pockets 74 or longitudinal slots 630 typically arranged in one or several rows on both sides of longitudinally extending channel 72 or slot 640. There are typically at least two and frequently at least three rows of staple pockets 74 or longitudinal slots 630 on each side of longitudinally extending channel 72 or slot 640, with staple pockets 74 or longitudinal slots 630 in each row typically staggered or offset relative to pockets or slots in the adjacent row, to improve the sealing and prevent leakage along the stapling line.

In the following description, descriptors and reference numerals associated with FIGS. 1-7 will be used for consistency, with the understanding that alternative structures such as these shown in FIG. 8 can also be used. Thus when referring to staple cartridge, reference numeral 70 of FIGS. 1-7 will be utilized, with the understanding that the disclosure is also applicable to staple cartridge 600 of FIG. 8.

Figure 9:
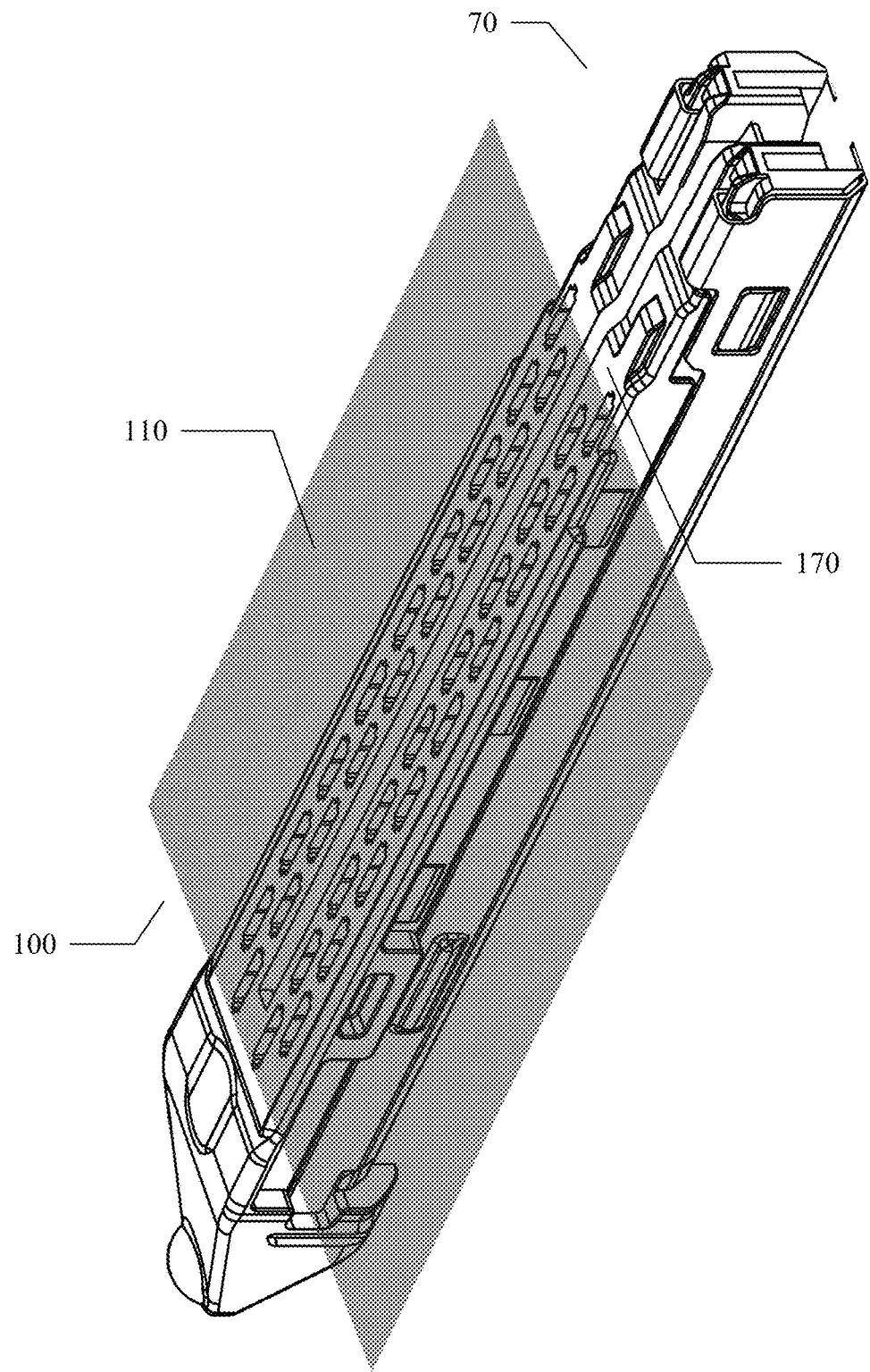
FIG. 9 shows a perspective view of an exemplary cartridge with a buttress in a flat unfolded configuration placed on top of tissue facing surface of the cartridge.
Figure 10:
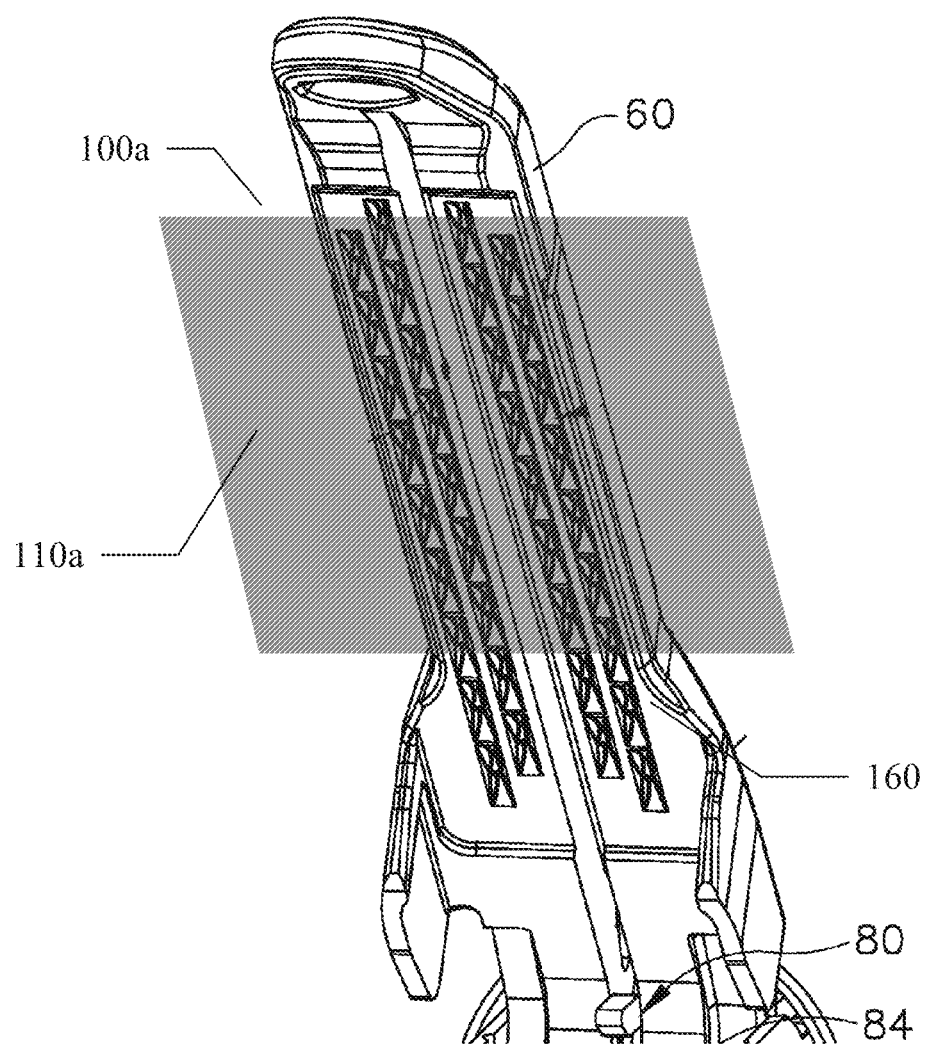
FIG. 10 shows a perspective view of an exemplary anvil with a buttress in a flat unfolded configuration placed on top of tissue facing surface of the anvil.

Referring now to FIGS. 9 and 10, according to the present invention, there is provided a buttress 100 or 100a, comprising absorbable or non-absorbable substantially flat and flexible material such as fabric, cloth, knit, felt, non-woven, foam, mesh, and the like, that is at least partially disposed on the tissue facing surface 170 of cartridge 70 or on tissue facing surface 160 of anvil 60 prior to stapling. Buttress 100 or 100a is shown for clarity semi-transparent, but it can be also opaque. In some embodiments, buttress 100 or 100a is substantially wider than the width of cartridge 70 tissue facing surface 170 or anvil 60 tissue facing surface 160, with the excess width of buttress 100 or 100a comprising a peripheral flap 110 or 110a. Buttress 100 or 100a is at least partially covering staple pockets 74 and preferably fully covering staple pockets 74.

Figure 11:
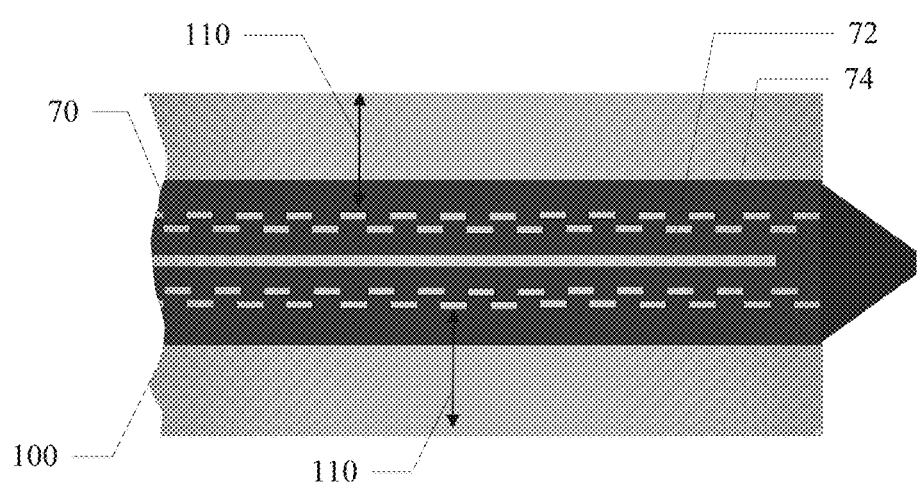
FIG. 11 shows a schematic top view of an exemplary cartridge with a buttress in a flat unfolded configuration placed on top of tissue facing surface of the cartridge.

Referring to FIG. 11, a simplified top view of cartridge 70 is presented with two rows of staple pockets 74 on each side of channel 72 and buttress 100 (shown for clarity semi-transparent) disposed on tissue facing surface 170, with essentially symmetrical arrangement of buttress 100 on top and around channel 72, with peripheral flaps 110 symmetrically extending on both sides of cartridge 70. Peripheral flaps 110 are schematically indicated by arrows showing the width of peripheral flaps 110, and showing a portion of buttress 100 that is foldable after deployment of staples.

Figure 12:
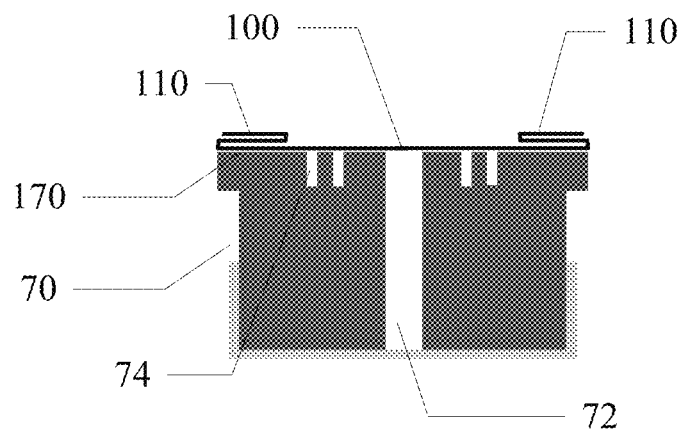
FIGS. 12-17 show a simplified cross-sectional view of cartridge with buttress disposed on tissue facing surface with flaps folded or rolled.
Figure 13:
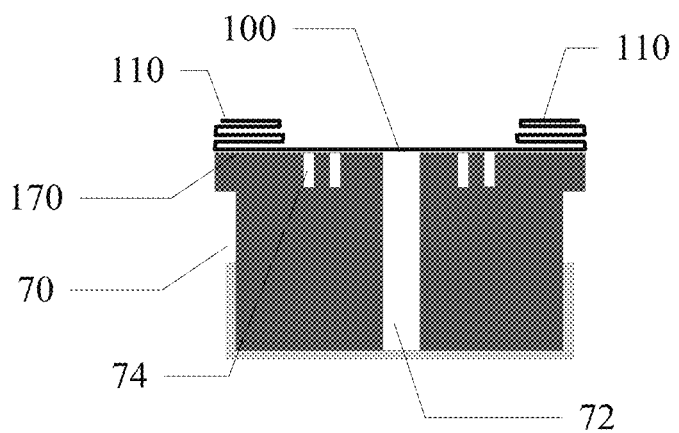
Figure 14:
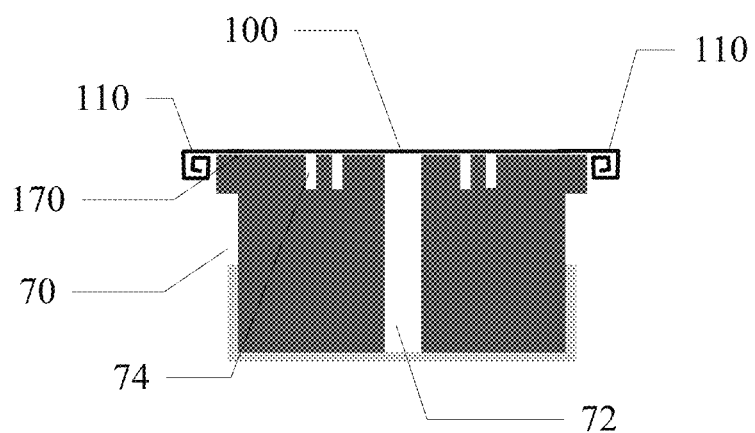
Figure 15:
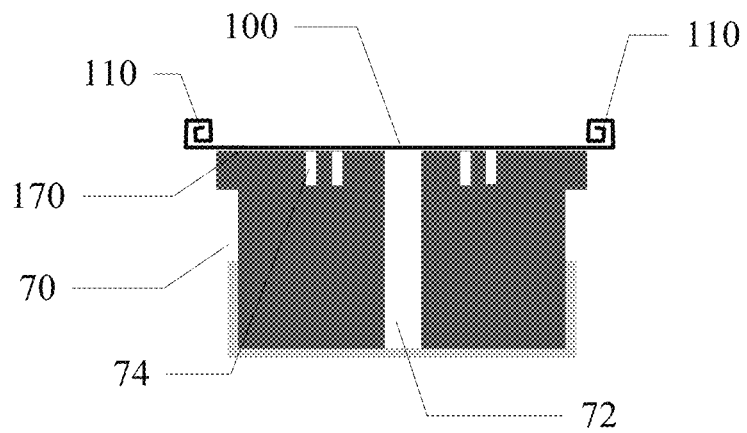
Figure 16:
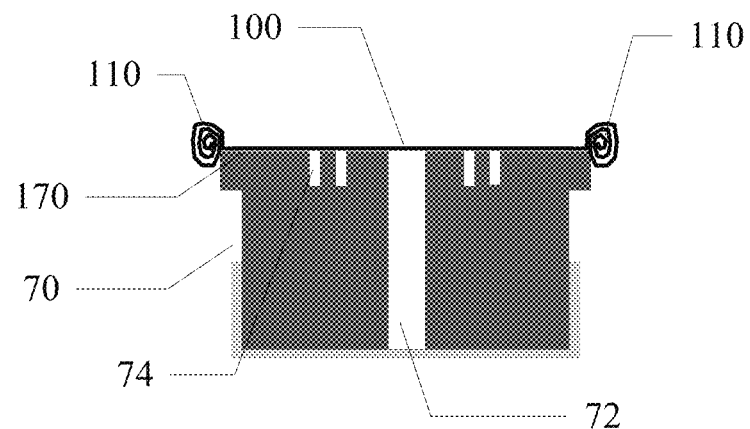
Figure 17:
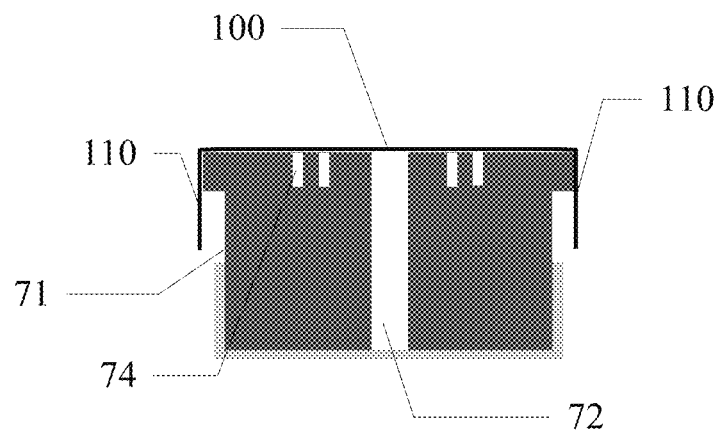

Referring to FIG. 12, a simplified front cross-sectional view of cartridge 70 is presented with two rows of staple pockets 74 on each side of channel 72 and buttress 100 disposed on tissue facing surface 170, with peripheral flaps 110 stored folded at least once back onto buttress 100 with no peripheral flap 110 being over any staple pockets 74, preventing stapling of peripheral flaps 110 upon deployment of staples (staples not shown for simplification) from staple pockets 74. Peripheral flap 110 is shown stored folded back twice onto buttress 100 and onto itself. Referring to FIG. 13, peripheral flap 110 is shown stored folded back four times onto buttress 100 and onto itself, or folded in an accordion-like shape. Any number of folds can be utilized to achieve necessary width of the buttress peripheral flap. Referring to FIGS. 14, 15, 16, peripheral flap 110 is shown stored rolled on itself in a roll positioned below or above tissue facing surface 170, or at about the level of tissue facing surface 170. Referring to FIG. 17, peripheral flap 110 is shown stored bent alongside cartridge body 71.

Figure 18:
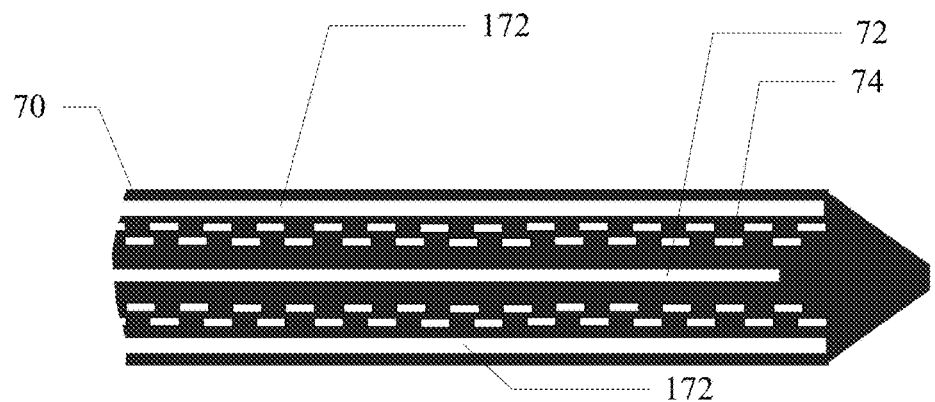
FIG. 18 shows a schematic top view of an exemplary cartridge having grooves in tissue facing surface for storing buttress flaps.
Figure 19:
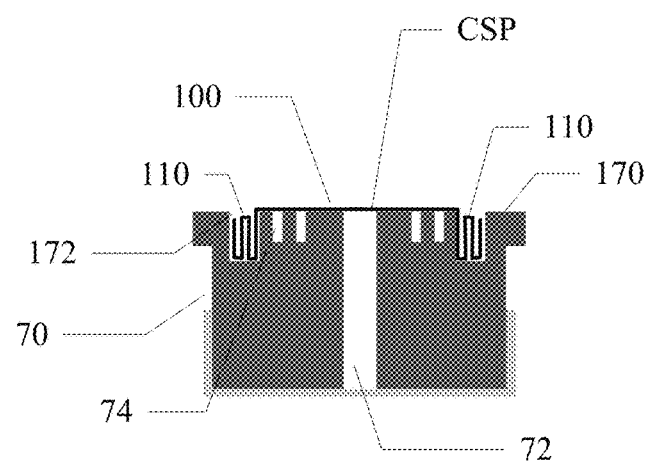
FIG. 19 shows a simplified cross-sectional view of cartridge with buttress disposed on tissue facing surface with flaps stored in the grooves.

Referring to FIGS. 18 and 19, an embodiment of cartridge 70 is shown with a longitudinal cavities or grooves or recesses 172 formed in cartridge 70 tissue facing surface 170, and running parallel to channel 72 on both sides of channel 72 on the periphery of tissue facing surface 170, with rows of staple pockets 74 being between longitudinal cavities or grooves 172 and channel 72. FIG. 18 shows no buttress 100 for simplification, but as can be seen in FIG. 19, buttress 100 peripheral flaps 110 are packed into cavities or grooves 172.

Figure 20:
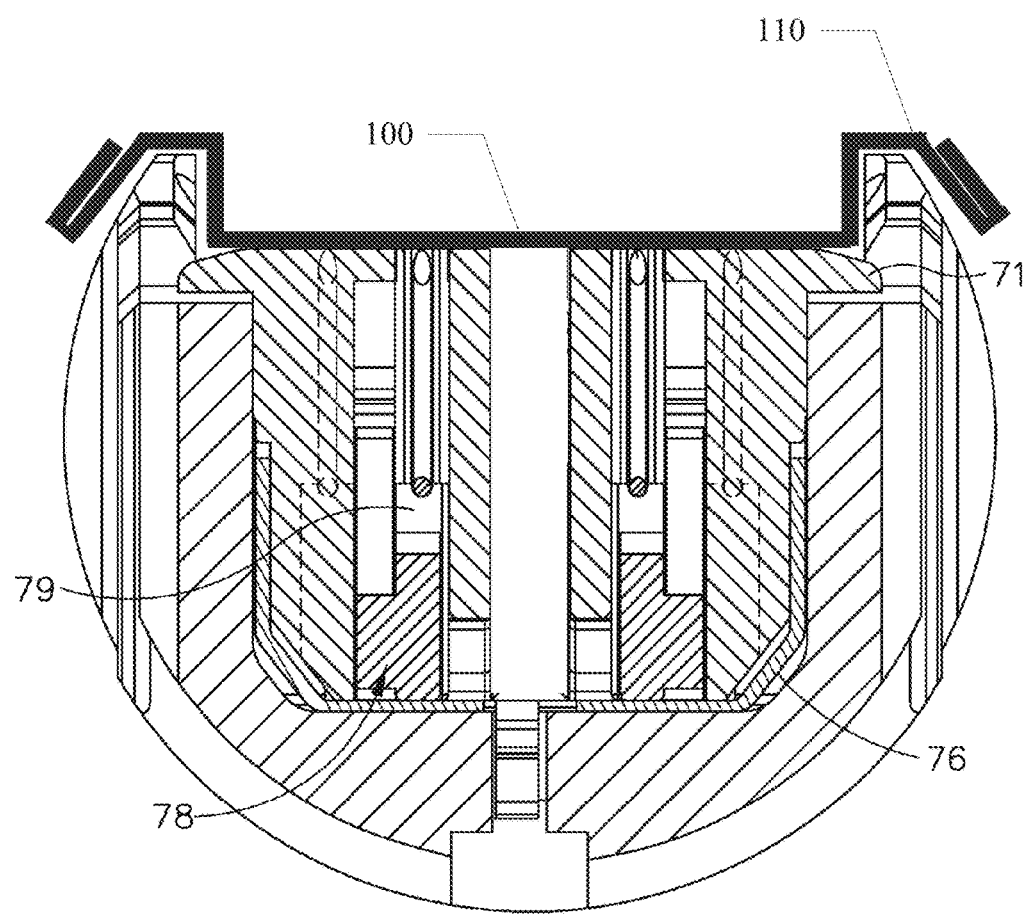
FIGS. 20-22 show cross sectional view of an exemplary cartridge within end-effector with a buttress shown schematically installed on the cartridge with flaps folded.
Figure 21:
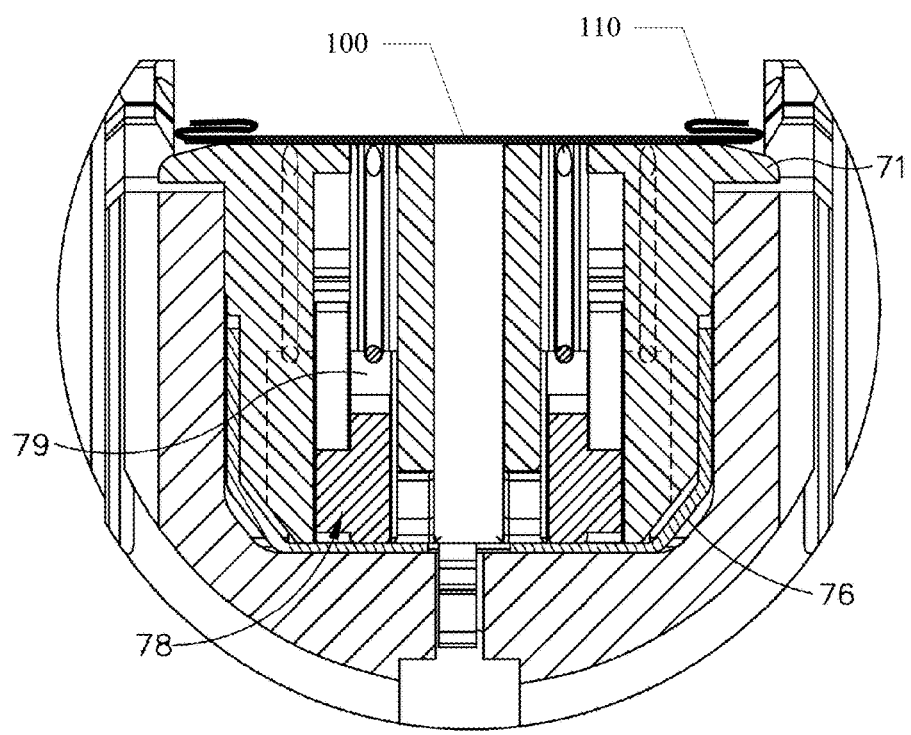
Figure 22:
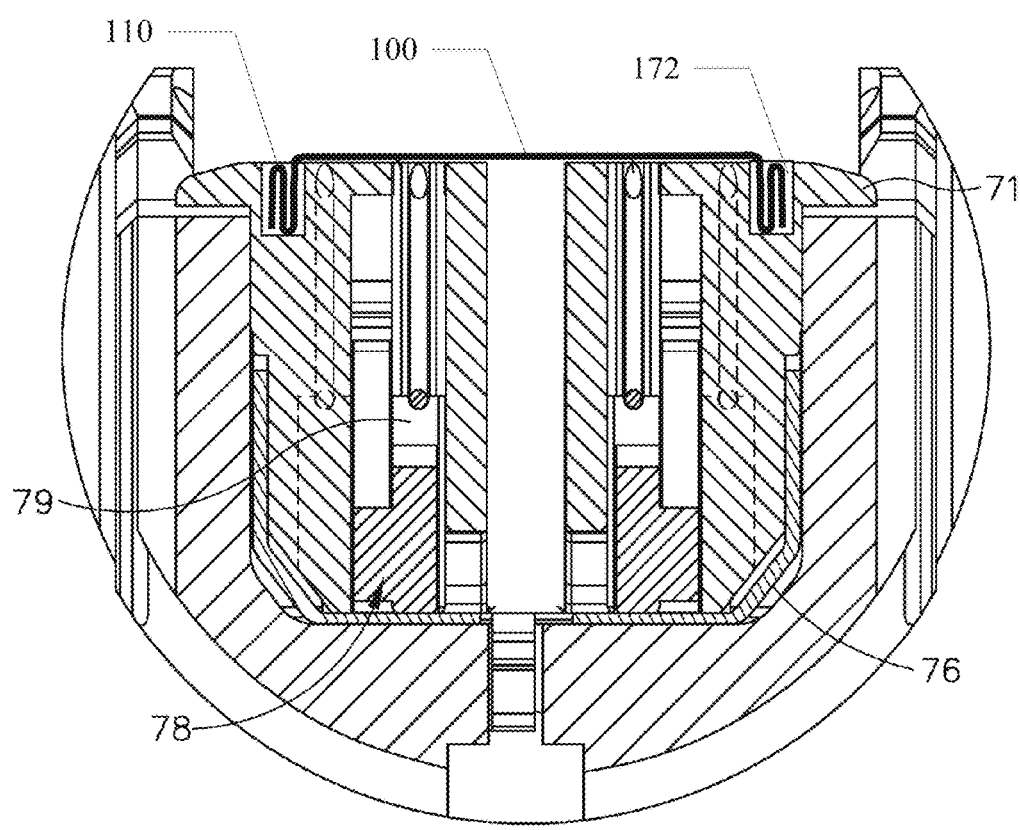

Referring now to FIGS. 20-22, representing, similarly to FIG. 6, a cross-sectional end view of the end effector of FIG. 3, taken along line 6-6 of FIG. 4, with the knife member 80 assembly not shown for simplification and buttress 100 with peripheral flaps 110 schematically shown. FIG. 20 is showing an embodiment similar to that of FIG. 15 or 17. FIG. 21 is showing an embodiment similar to that of FIG. 12 or 13. FIG. 22 is showing an embodiment similar to that of FIG. 19.

In all embodiments, peripheral flaps 110 are stored outside of staple pockets 74 to prevent stapling of peripheral flaps 110 during staple deployment. Peripheral flaps 110 are stored distal to channel 72 and opposite channel 72, on the periphery of cartridge 70, with staple pockets 74 being between peripheral flaps 110 and channel 72.

Peripheral flap 110 is stored prior to the deployment/folding over tissue resected edge by being rolled on itself in one or more turns; folded in an accordion-like shape in one or more layers, folded onto cartridge 70 in one or more layers, or similarly packed for ease of later unfurling.

Figure 23:
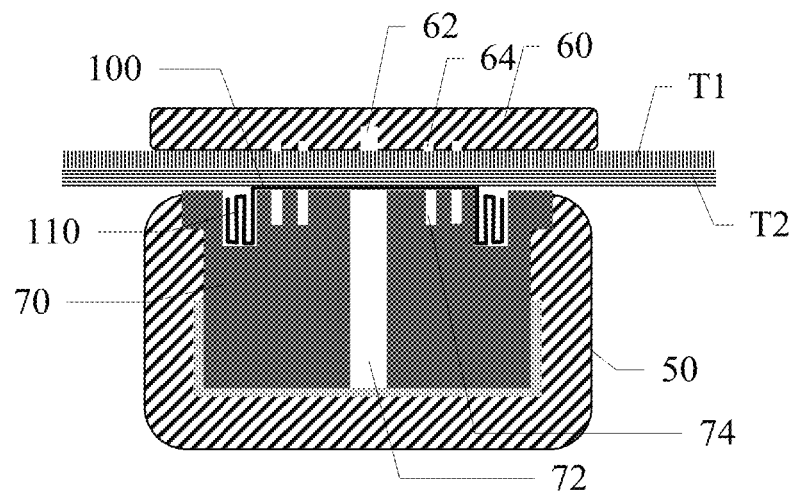
FIG. 23 shows a simplified cross-sectional view of tissue positioned prior to stapling and resection between anvil and cartridge installed in the end effector.

Referring to FIG. 23, a simplified cross-sectional view is presented of to be resected and stapled tissue layers T1 and T2 compressed between lower jaw 50 with cartridge 70 and anvil 60. Cartridge 70 is shown with buttress 100 disposed on cartridge 70 and in contact with tissue T2, with peripheral flaps 110 packed into grooves 172 as was shown in the embodiment of FIG. 19. Clearly, any other arrangement of peripheral flaps 110 outside of staple pockets 74 can be utilized. The arrangement in FIG. 23 is corresponding to position immediately prior to deploying staples 77 (not shown in FIG. 23) and driving staples 77 through tissues T1 and T2 into anvil 60 and also prior to the knife member 80 (not shown in FIG. 23) translating through channel 72 and resecting stapled tissues T1 and T2.

Figure 24:
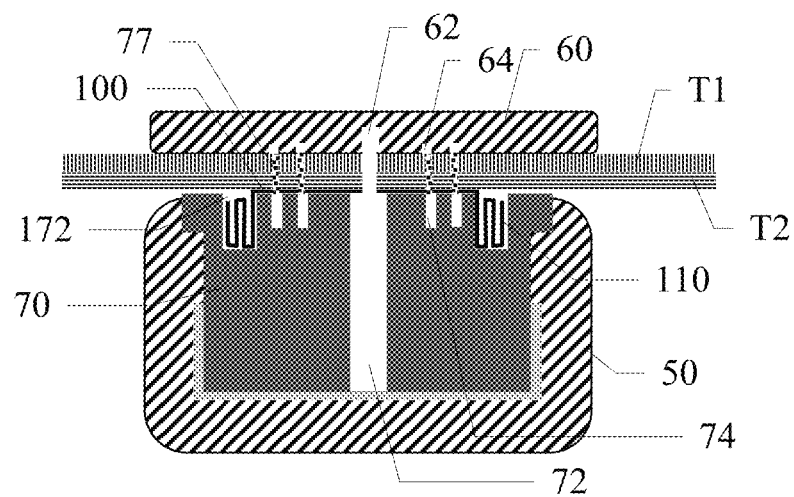
FIG. 24 shows the view of FIG. 23 after resection and stapling.

Referring to FIG. 24, a simplified cross-sectional view is presented of the position after deployment of staples 77 and resecting tissue layers T1 and T2. Buttress 100 is stapled to the tissues T1 and T2 by staples 77 and is cut into two halves by the action of knife member 80 (not shown in FIG. 23) as knife member 80 resects/cuts tissue.

Figure 25:
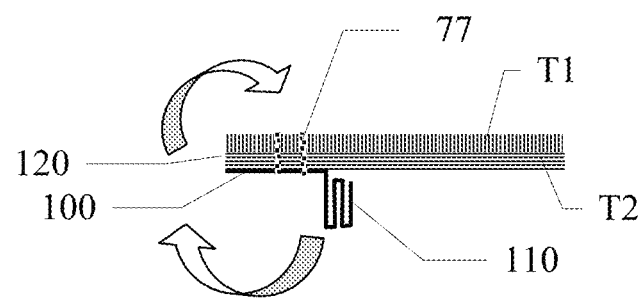
FIGS. 25-28 show schematic cross-sectional views of tissue and buttress after stapling and removal of the surgical stapler, illustrating unfurling and wrapping flaps around resected surface and opposing tissue surface.

Referring to FIG. 25, a simplified cross-sectional view is presented of the position after opening of stapler 10 i.e. separation of lower jaw 50 and anvil 60 after stapling and removal of stapler 10. Buttress 100 remains attached to stapled and resected tissues T1 and T2 by staples 77. Buttress 100 with peripheral flap 110 has separated from cartridge 70, with peripheral flap 110 moving from its storage position within groove 172. Only one side of resected tissue layers T1 and T2 is shown for simplification. Tissue layers T1 and T2 have formed an exposed resection edge 120.

Figure 26A:
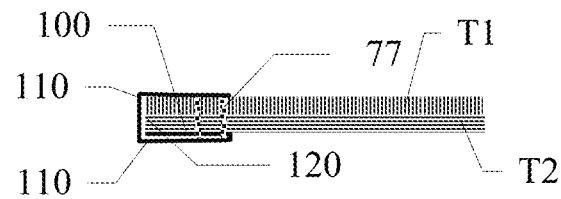

Peripheral flap 110 is then unfurled from its folded storage position and flipped over or folded back and is wrapped around the resected edge 120, as schematically indicated by arrows in FIG. 25, resulting in the position of the peripheral flap 110 shown in FIG. 26A. As can be seen, peripheral flap 110 starts folding at stapled area of buttress 100, i.e. at staples 77 row farthest away from edge 120.

Peripheral flap 110 is covering the stapled area of buttress on tissue T2, edge 120, and at least a portion of tissue T1. Advantageously, peripheral flap 110 of buttress 100 is covering the resected edge 120 which will help hemostasis and tissue sealing, improve healing, prevent adhesions. Buttress 100 is contacting tissue T2 with one surface of the buttress, and is contacting edge 120 and tissue T1 with an opposite surface of buttress 100. In some embodiments, such as one shown in FIG. 26, peripheral flap 110 is covering the stapled area of tissue T1 and beyond. In some embodiments, such as one shown in FIG. 27, peripheral flap 110 is covering only a small portion of tissue T1 and not covering the stapled area of tissue T1.

Peripheral flap 110 is contacting tissue edge 120 and opposing tissue T1 with the side of buttress 100 that is not in contact with tissue T1, in other words with the side of buttress 100 that is opposite to the side of the buttress in contact with tissue T1.

Peripheral flap 110 is manipulated by the surgeon using any available tools such as surgical grasper, or manually.

The above operating description was provided for embodiments of FIGS. 19, 22, however it should be understood that a similar operation sequence and positions will result for other embodiments of the present invention, i.e. for other arrangements of peripheral flap 110 storage on anvil 60 or on cartridge 70.

Figure 26B:
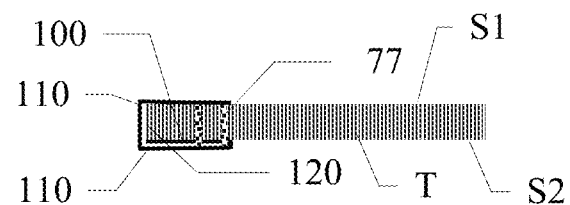

The above description was provided mostly referencing joining and resecting two layers of tissue T1 and T2. However, the same operating and structural approach is applicable to joining more than two tissue layers, or to resecting and closing one tissue layer. Referring to FIG. 26B, a position similar to FIG. 26A is presented, with the difference being that only one tissue layer, designated as T and having surfaces S1 and S2 in FIG. 26B, is being resected and stapled, with surface S2 corresponding to tissue T2 and surface S1 corresponding to tissue T1.

In some embodiments, optional fixating means are provided for peripheral flap 110 fixating on edge 120, and/or, on tissue T1. In more preferred embodiments, peripheral flap 110 has means for fixation on at least tissue T1.

Figure 27:
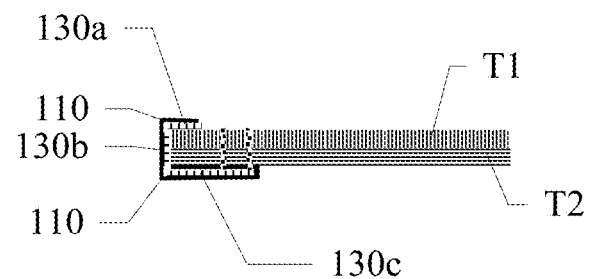

Referring to FIG. 27, in one embodiment, there is provided an adhesive coating or adhesive layer 130 on buttress 100 side facing away from tissue T2, with at least adhesive layer 130a on periphery of peripheral flap 110 which is in contact with tissue T1. Optionally there also can be adhesive layer 130b on area of peripheral flap 110 in contact with edge 120. Optionally there also can be adhesive layer 130c on area of peripheral flap 110 in contact with stapled area of buttress 100. Optionally, all buttress 100 side facing away from tissue T2 can be covered by adhesive layer (not shown).

As peripheral flap 110 is folded over the resected edge and brought into contact with tissue T1, peripheral flap 110 is secured to tissue edge 120 and/or to tissue T1 by the action of the adhesive layer 130. A number of biocompatible tissue adhesives and sealants, which are activated by moisture, blood, and/or by contact with wet tissue are known and can be utilized. Such biocompatible adhesives include, for example, fibrin glue, various cross-linking agents, alone or in combination with additional agent such as a protein and are known to a skilled artisan.

U.S. Pat. No. 6,458,147 "Compositions, systems, and methods for arresting or controlling bleeding or fluid leakage in body tissue" discloses biocompatible and biodegradable hydrogel compound applied to arrest the flow of blood or fluid from body tissue. The compound preferably includes a protein comprising albumin, which is mixed with a polymer that comprises poly(ethylene) glycol (PEG), and, most preferably, a multi-armed PEG polymer.

U.S. Patent Publication No. 2006/0062768 "Biocompatible hydrogel compositions" discloses biocompatible synthetic electrophilic component mixed with a nucleophilic component. The electrophilic component can include a functionalized electrophilic poly (anhydride ester) material. The nucleophilic material can include a protein. The components can react by cross-linking when exposed to moisture.

U.S. Patent Publication No. 2011/0104280 "Wound treatment systems, devices, and methods using biocompatible synthetic hydrogel compositions" discloses a multi-arm poly (ethylene glycol) (PEG) succinimidyl glutarate is mixed with a biocompatible, synthetic, nucleophilic polymer component essentially free of albumin and other biological molecules, containing, e.g., a polypeptide moiety having a number of active surface lysines of at least twenty per 5000 M/W, which can also be blended with a multi-arm poly (ethylene glycol) (PEG) amine.

U.S. Patent Publication No. 2014/0369991A1 "Formulations for Wound Therapy" discloses formulations comprising a dry powder fibrin sealant comprised a mixture of fibrinogen and/or thrombin, for use in the treatment of wounds or injuries, in particular for use as a topical hemostatic composition or for surgical intervention.

The above cited patents and patent applications are incorporated by reference herein.

In one embodiment, adhesive is formed from dry protein such as albumin and a crosslinking agent. The cross-linking agent is exemplified by 4 arm polyethylene glycol succinimidyl glutarate (also referred to as PEG-SG4, succinimidyl PEG NHS, tetra functional poly (ethylene glycol) succinimidyl glutarate). Protein and cross-linking agent are disposed on or impregnated into peripheral flap 110 forming adhesive layer 130a, 130b, 130c, or adhesive layer on all buttress 100 side facing away from tissue T2 upon exposure to moisture or blood. Adhesive is activated upon exposure to moisture or blood resulting in adhesive attachment of peripheral flap 110 to edge 120 and/or tissue T1.

In one embodiment, adhesive is formed from dry precursors to fibrin glue, such as fibrinogen and thrombin, which are disposed on or impregnated into peripheral flap 110 forming adhesive layers 130a, 130b, 130c, or adhesive layer on all buttress 100 side facing away from tissue T2 upon exposure to moisture or blood. Upon contact with moisture, fibrin is formed resulting in adhesive attachment of peripheral flap 110 to edge 120 and/or tissue T1.

Figure 28:
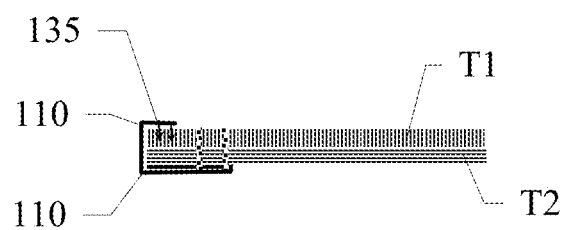

According to one embodiment shown in FIG. 28, one or more miniature anchors such as barbed pins 135 are provided on peripheral flap 110 in the area on periphery of peripheral flap 110 which is in contact with tissue T1 and corresponds to area 130a in FIG. 27.

According to one embodiment, peripheral flap 110 is made of a material that is self-adhering to wet tissue surfaces, such as dry collagen foam, ORC sheet, PEG-SG coated bio-absorbable sheet, fibrinogen and or thrombin coated sheet, natural or natural synthetic composite material such as gelatin, chitosan, etc., and combinations thereof. Other materials can be utilized.

According to another embodiment, peripheral flap 110 is coated by a moisture activated composition having high adherence to wet tissues, such as a mucoadhesive composition.

Figure 29A:
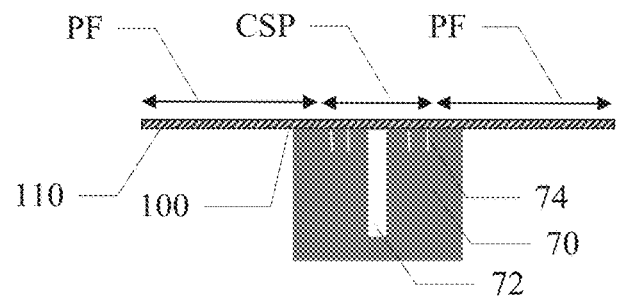
FIGS. 29A-F show schematic cross-sectional views of embodiments of single layer and multi-layer buttress on a cartridge.

Referring now to FIG. 29A, a schematic cross-sectional view of buttress 100 is presented disposed in unfurled and straightened configuration on cartridge 70. The width of a central stapled portion or area of buttress 100 which will be stapled by staples (not shown) in staple pockets 74, is designated by arrow "CSP" and indicates central stapled portion of buttress 100. The width of peripheral flaps 110 of buttress 100 located on the periphery of buttress 100, which peripheral flaps 110 are not stapled, is designated by arrows "PF" and indicates peripheral flap width. Upon stapling and resection, buttress 100 is cut along channel 72 in half and entire peripheral flap 110 width PF can be folded backwards and wrapped around resected tissue (not shown). Peripheral flap 110 width PF is defined as area of buttress 100 distal to channel 72 that is not stapled and can be folded over stapled portion of buttress.

The width of central stapled portion of buttress 100, 100a is configured so that this portion is covering stapled area or covering staple pockets 74 or staple forming pockets 64. In some embodiments, the width of central stapled portion of buttress 100, 100a is from about 0.5 to about 1.0 times the width of tissue facing surface 170 or 160, such as 0.7, 0.8, 0.9, 1.0 times the width of tissue facing surface 170 or 160.

The width of peripheral flaps 110, 110a is configured so that peripheral flaps can be folded backwards and wrapped around resected tissue edge 120. In some embodiments, the width of each peripheral flap is at least equal to or larger than one half of the width of tissue facing surface 170 or 160, such as 0.6, 0.7, 0.8, 0.9, 1, 1.2, 1.5, 2 times the width of tissue facing surface 170 or 160.

Still referring to FIG. 29A, in one embodiment, buttress 100 comprises a single layer of uniform thickness material. In alternative embodiments, and referring now to FIGS. 29B-F, buttress 100 comprises a multilayer material or single layer material of non-uniform thickness.

Figure 29B:
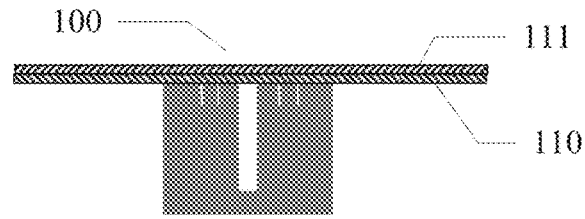
Figure 30A:
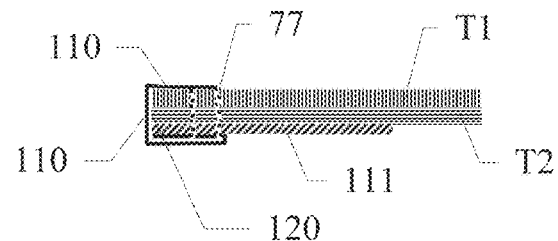
FIGS. 30A-E shows schematic cross-sectional views of tissue and two-layer buttress after stapling and removal of the surgical stapler, illustrating unfurling and wrapping flaps around resected surface and opposing tissue surface.

Referring to FIG. 29B, in one embodiment, buttress 100 comprises a two-layer construct, with peripheral flaps 110 facing cartridge 70 and adapted to be wrapped around tissue edge, while second layer 111 of buttress 100, optionally less flexible, and optionally thicker material, is optimized for tissue support and/or staple line reinforcement, is adapted to remain opposite tissue T2. FIG. 30A shows embodiment of FIG. 29B after stapling and resection, with peripheral flap 110 wrapped around tissues and positioned on tissue T1, with second layer 111 remaining in contact with tissue T2 after stapling. Advantageously, there is provided tissue support and/or staple line reinforcement by layer 111 and simultaneously coverage of resected edge 120 by peripheral flap 110. Thus only the flexible peripheral flap 110 disposed immediately facing cartridge 70 is folded back over the resected edge; the second layer 111 is used to reinforce the stapled tissue.

Figure 29C:
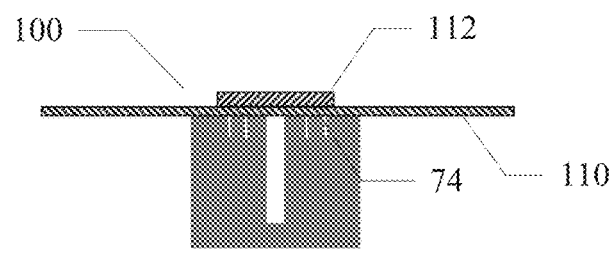
Figure 30B:
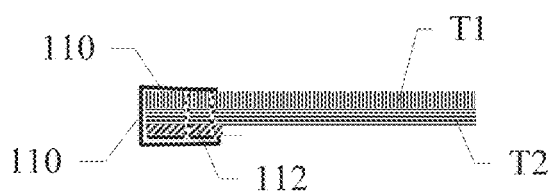

Referring to FIG. 29C, in one embodiment, buttress 100 comprises a two-layer construct, with peripheral flaps 110 facing cartridge 70 and adapted to be wrapped around tissue edge, while second layer 112 of buttress 100, optionally less flexible and optionally thicker material, is optimized for staple line reinforcement and/or tissue thickness compensation, and is adapted to be stapled and remain opposite tissue T2. FIG. 30B shows embodiment of FIG. 29C after stapling and resection, with peripheral flap 110 wrapped around tissues and positioned on tissue T1, with second layer 112 remaining in contact with tissue T2 after stapling. Advantageously, there is provided staple line reinforcement and/or tissue thickness compensation by layer 112 and simultaneously coverage of resected edge 120 by peripheral flap 110. Thus only the flexible peripheral flap 110 disposed immediately facing cartridge 70 is folded back over the resected edge; the second layer 112 is used to reinforce the stapled tissue. The width of second layer 112 is as shown, at least wide enough to cover the stapled area i.e. area between outermost rows of staple pockets 74. Alternatively (not shown), the width of second layer 112 is equivalent or slightly wider than cartridge 70.

Figure 29D:
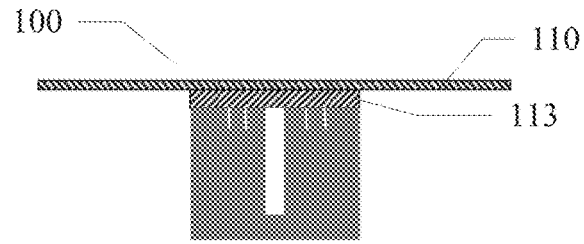
Figure 30C:
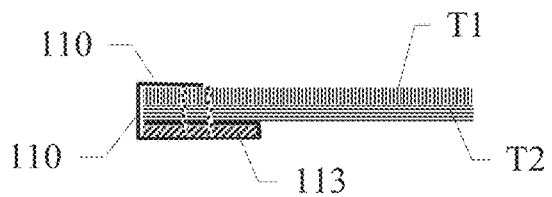

Referring to FIG. 29D, in one embodiment, buttress 100 comprises a two-layer construct, with second layer 113 of buttress 100, facing cartridge 70 and optimized for staple line reinforcement and/or tissue thickness compensation, is adapted to be stapled and remain opposite tissue T2. Second layer 113 is positioned between cartridge 70 and peripheral flaps 110, which are adapted to be wrapped around tissue edge. FIG. 30C shows embodiment of FIG. 29D after stapling and resection, with peripheral flap 110 wrapped around tissues and positioned on tissue T1, with second layer 112 remaining in contact with tissue T2 after stapling. Advantageously, there is provided staple line reinforcement and/or tissue thickness compensation by layer 112 and simultaneously coverage of resected edge 120 by peripheral flap 110. Thus only the flexible peripheral flap 110 is folded back over the resected edge; the second layer 112 is used to reinforce the stapled tissue. The width of second layer 113 is as shown, is substantially equivalent to width of cartridge 70. Alternatively (not shown), the width of second layer 113 is at least wide enough to cover the stapled area i.e. area between outermost rows of staple pockets 74.

Figure 29E:
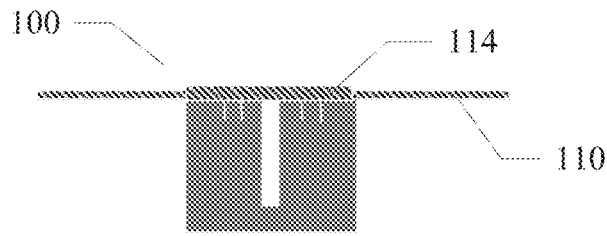
Figure 30D:
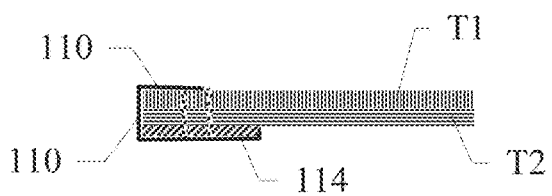

Referring to FIG. 29E, in one embodiment, buttress 100 comprises a construct made of the same material and having a central thicker area 114 optimized for staple line reinforcement and/or tissue thickness compensation, adapted to be stapled and remain opposite tissue T2. Peripheral flaps 110, positioned on two sides of central thicker area 114, are adapted to be wrapped around tissue edge. FIG. 30D shows embodiment of FIG. 29E after stapling and resection, with peripheral flap 110 wrapped around tissues and positioned on tissue T1, with central thicker area 114 remaining in contact with tissue T2 after stapling. Advantageously, there is provided staple line reinforcement and/or tissue thickness compensation by area 114 and simultaneously coverage of resected edge 120 by peripheral flap 110. The width of central thicker area 114 is as shown, substantially equivalent to width of cartridge 70. Alternatively (not shown), the width of central thicker area 114 is at least wide enough to cover the stapled area i.e. area between outermost rows of staple pockets 74.

Figure 29F:
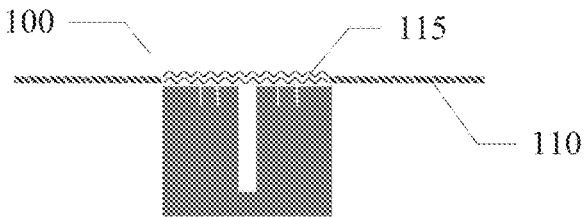
Figure 30E:
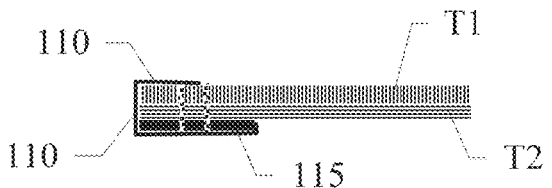

Referring to FIG. 29F, in one embodiment, buttress 100 comprises a construct having a central thicker area 115 made of a first material, optimized for staple line reinforcement and/or tissue thickness compensation, adapted to be stapled and remain opposite tissue T2. Peripheral flaps 110, positioned on two sides of central thicker area 115, are made of a second material joined to the first material, and are adapted to be wrapped around tissue edge. FIG. 30E shows embodiment of FIG. 30E after stapling and resection, with peripheral flap 110 wrapped around tissues and positioned on tissue T1, with central thicker area 115 remaining in contact with tissue T2 after stapling. Advantageously, there is provided staple line reinforcement and/or tissue thickness compensation by area 115 and simultaneously coverage of resected edge 120 by peripheral flap 110. The width of central thicker area 115 is as shown, substantially equivalent to width of cartridge 70. Alternatively (not shown), the width of central thicker area 115 is at least wide enough to cover the stapled area i.e. area between outermost rows of staple pockets 74.

Figure 31:
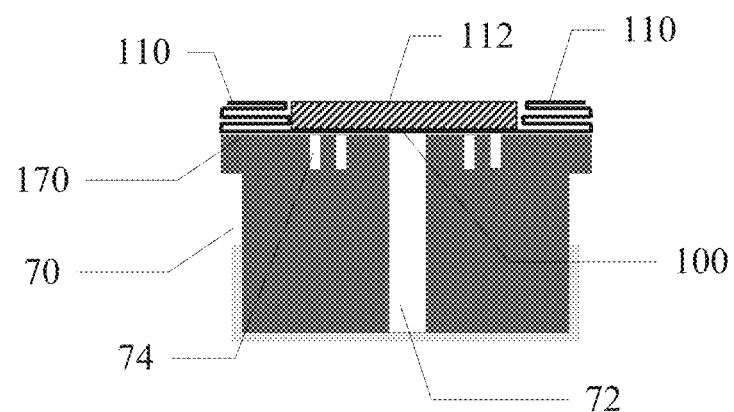
FIGS. 31 and 32 show a simplified cross-sectional view of cartridge with two-layer buttress disposed on tissue facing surface with flaps folded.

Referring to FIG. 31, a simplified frontal cross-sectional view of an embodiment of cartridge 70 is presented with two rows of staple pockets 74 on each side of channel 72 and buttress 100 of embodiment shown in FIG. 29C disposed on tissue facing surface 170, with peripheral flaps 110 stored folded onto buttress 100 and onto itself. Buttress 100 comprises a two-layer construct, with peripheral flaps 110 facing cartridge 70 and adapted to be wrapped around tissue edge, while second layer 112 of buttress 100, optionally less flexible material, is optimized for staple line reinforcement and/or tissue thickness compensation.

Figure 32:
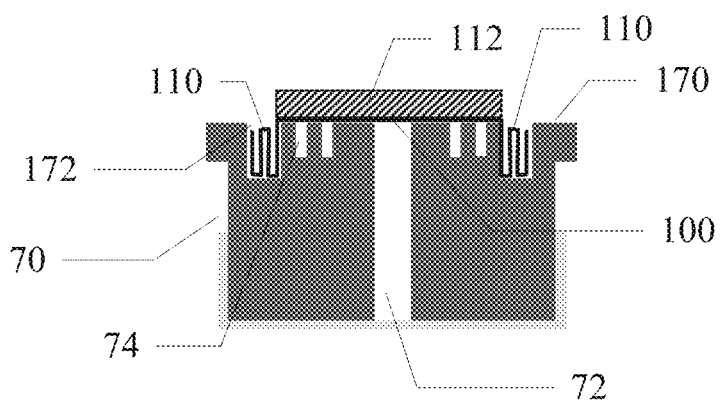

Referring to FIG. 32, a simplified frontal cross-sectional view of an embodiment of cartridge 70 with longitudinal grooves 172 is shown. Buttress 100 of embodiment shown in FIG. 29C is disposed on tissue facing surface 170, with peripheral flaps 110 packed into grooves 172. Buttress 100 comprises a two-layer construct, with peripheral flaps 110 adapted to be wrapped around tissue edge, while second layer 112 of buttress 100, optionally less flexible material, is optimized for staple line reinforcement and/or tissue thickness compensation.

In certain embodiments, there is provided a buttress 100a supported on anvil 60.

Figure 33:
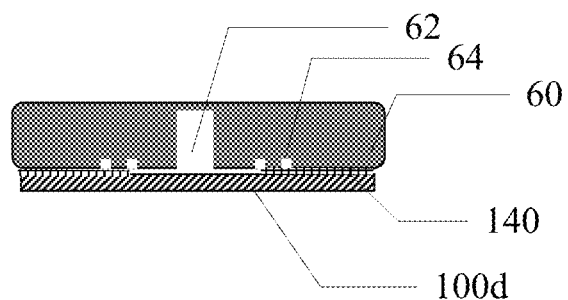
FIGS. 33-35 show several configurations of buttress positioned on the anvil.

Referring to FIG. 33, a simplified cross-sectional view of anvil 60 is sown, with buttress 100d, in one embodiment, supported on anvil 60 in addition to buttress 100 supported on cartridge 70 described above. In this embodiment, buttress 100d has no flaps and has a width substantially the same as width of anvil 60. Buttress 100d has adhesive 140 is disposed on the side of buttress 100d facing anvil 60 and staple forming pockets 64. Upon deployment of both buttress 100d and buttress 100 onto stapled tissues T1 and T2, adhesive 140 can be used to adhesively fixate buttress 100 peripheral flap 110 on buttress 100d.

Figure 34:
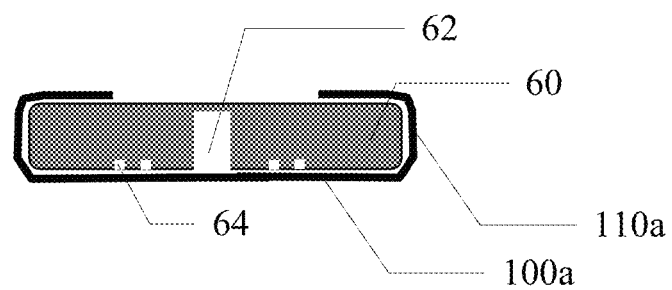

Referring to FIG. 34, a simplified cross-sectional view of anvil 60 is shown, with buttress 100a, in one embodiment, supported on anvil 60 as optional alternative to or supplementing buttress 100 supported on cartridge 70 described above. In this embodiment, buttress 100a has peripheral flaps 110a which are wrapped around anvil 60 prior to deployment.

Figure 35:
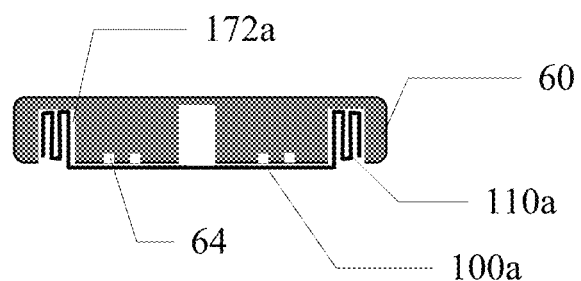

Referring to FIG. 35, a simplified cross-sectional view of anvil 60 is shown, with buttress 100a, in one embodiment, supported on anvil 60 as optional alternative to or supplementing buttress 100 supported on cartridge 70 described above. In this embodiment, buttress 100a has peripheral flaps 110a which are packed into longitudinal cavities or grooves 172a formed in anvil 60, and running parallel to channel 62 on both sides of channel 62 on the periphery of anvil 60 as shown, with rows of staple forming pockets 64 being between longitudinal cavities or grooves 172a and channel 62.

In operation, buttress 100a is stapled to tissues T1 and T2 and is cut into two halves by the action of knife member 80 as knife member 80 resects/cuts tissue. After stapling and removal of stapler 10, buttress 100a remains attached to stapled and resected tissues T1 and T2, with peripheral flaps 110a separating from anvil 60. Peripheral flap 110a is then unfurled from its folded storage position and flipped over or folded back and is wrapped around the resected edge.

The above description mostly concentrated on peripheral flaps 110, 110a of buttress 100 and 100a positioned on the periphery of buttress 100 or 100a and surrounding central stapled portion CSP of buttress, with peripheral flaps stored distal to longitudinally extending channels 72 or 62, on the periphery of tissue facing surface 170 of cartridge 70 or 160 or anvil 60.

In the alternative embodiments of the present invention described below, central flaps (CF) 105 or 105a portions of buttress 100 or 100a are positioned proximal to channel 72, i.e. between channel 72 and rows of staple pockets 74 or channel 62 and rows of staple forming pockets 62.

Figure 36A:
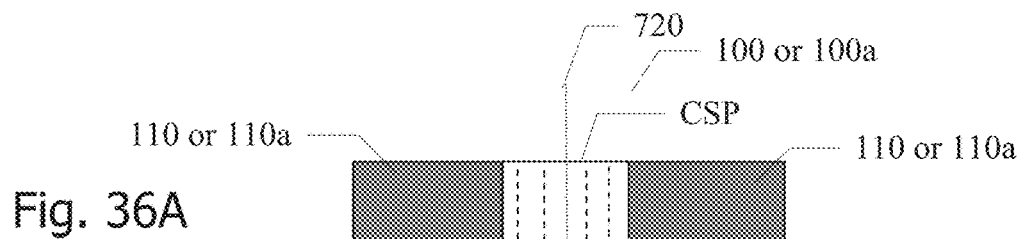
FIGS. 36A-D shows schematic top views of buttress with peripheral flaps and buttress with central flaps, with flaps shown in flat planar view and also in folded view.
Figure 36B:
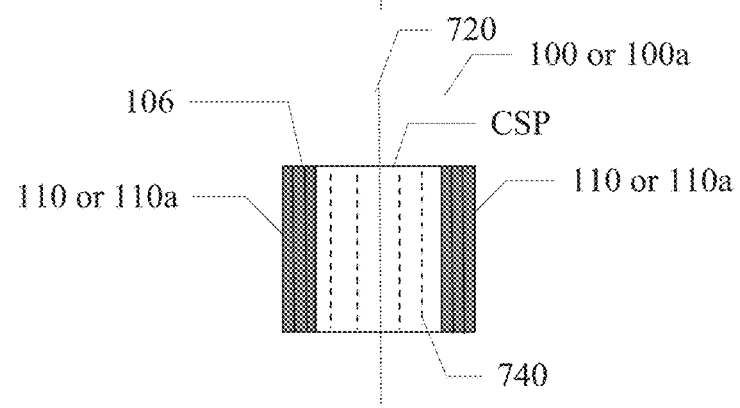

Referring to FIGS. 36A and 36B, for comparative purposes, a schematic top view of buttress 100 or 100a with peripheral flaps 110, 110a. FIG. 36A shows buttress 100, 100a in flat, unpacked/unwrapped view prior to stapling and resection, with peripheral flaps 110 or 110a forming a peripheral portion of buttress 100 or 100a, with also schematically shown line of resection 720 and stapling lines 740.

FIG. 36B shows schematic top view of buttress 100 or 100a presented in packed/wrapped configuration prior to stapling and resection, with buttress peripheral flaps 110 or 110a folded and packed in the peripheral area outside of stapling lines 740 and distal to line of resection 720. Folds 106 of peripheral flaps 110, 110a are schematically shown.

Figure 36C:
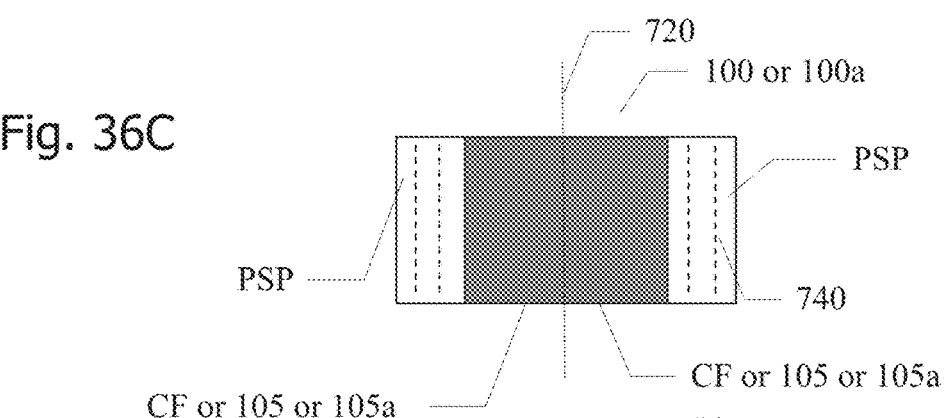
Figure 36D:
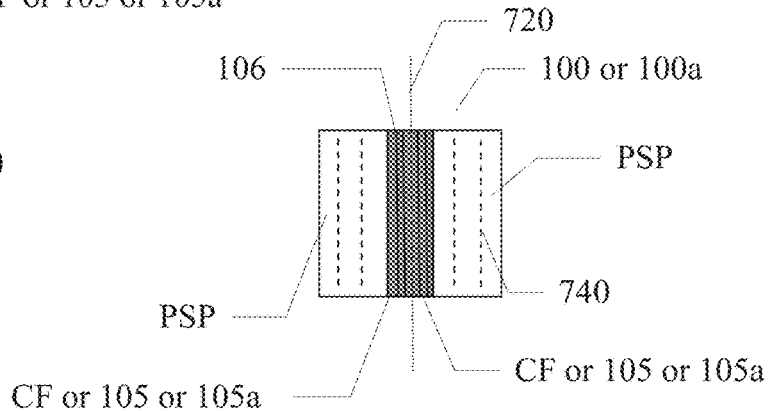

Referring to FIGS. 36C, 36D, embodiments of the present invention are shown where central flaps (CF) 105 or 105a are forming central portion of buttress 100 or 100a, while peripheral stapled portion (PSP) of buttress 100 or 100a is located on the periphery of buttress 100 or 100a. FIGS. 36C, 36D are also schematically presenting line of resection 720 and stapling lines 740.

FIG. 36C shows a schematic top view of buttress 100 or 100a in unpacked/unwrapped view. FIG. 37D shows a schematic top view of buttress 100 or 100a in packed/wrapped configuration prior to stapling and resection, with buttress central flaps 105 or 105a folded and packed in the area between line of resection 720 and stapling lines 740. Folds 106 of central flaps 105 or 105a are schematically shown.

Figure 37:
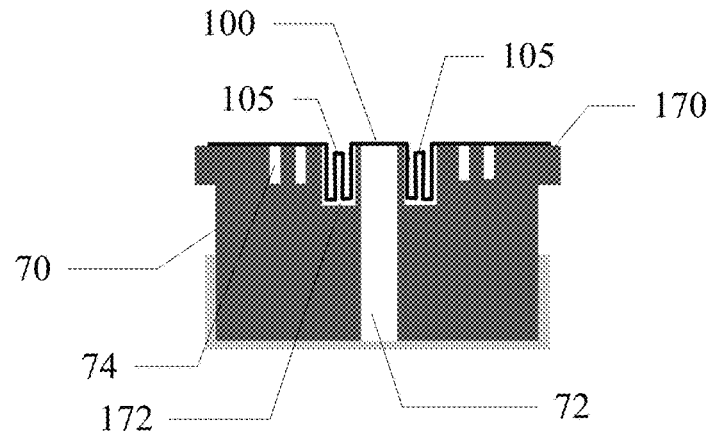
FIGS. 37-39 show schematic cross sectional views of cartridge with a buttress having central flaps.

FIG. 37 shows a schematic cross-sectional view of cartridge 70 with buttress 100, with central flaps 105 folded and packed into grooves 172 which are proximal to channel 72 on both sides of channel 72, i.e. between channel 72 and rows of staple pockets 74.

Figure 38:
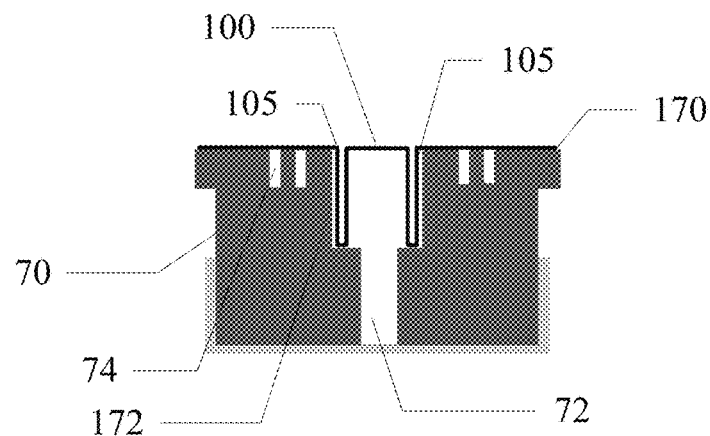

FIG. 38 shows an alternative embodiment whereby grooves 172 are open on one side to channel 72.

Figure 39:
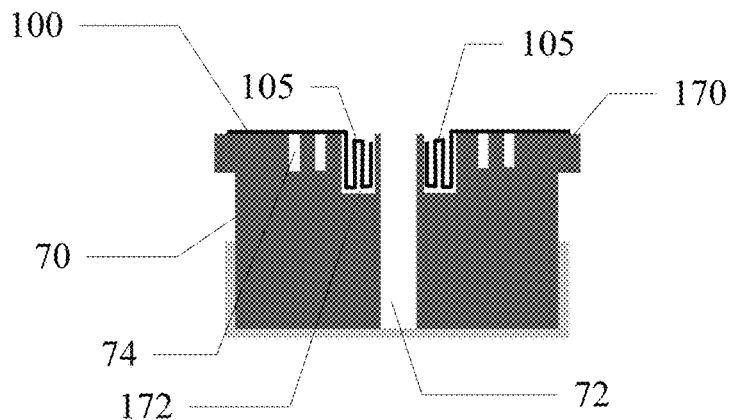

FIG. 39 shows an alternative embodiment whereby buttress 100 is pre-cut into two halves positioned on both sides of channel 72.

Figure 40:
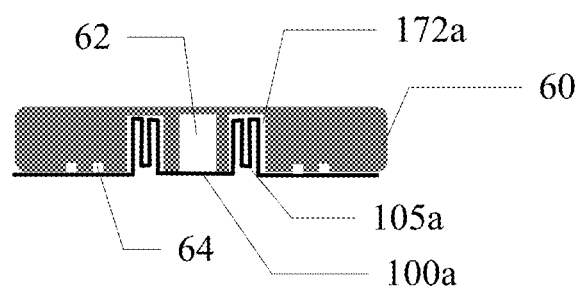
FIGS. 40 and 41 show schematic cross sectional views of anvil with a buttress having central flaps.
Figure 41:
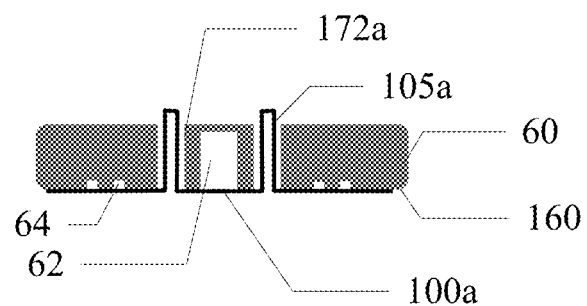

Similarly, as applicable to anvil 60 and buttress 100a, embodiments shown in FIGS. 40-41 present schematic cross-sectional views of anvil 60 with buttress 100a, central flaps 105a of buttress 100a are positioned proximal to channel 62, i.e. between channel 62 and rows of staple forming pockets 64. Central flaps 105a of these embodiments are formed in the central portion of buttress 100a.

FIG. 40 shows central flaps 105a folded and packed into grooves 172a which are proximal to channel 62 on both sides of channel 62, i.e. between channel 62 and rows of staple forming pockets 64.

FIG. 41 shows an alternative embodiment whereby grooves 172a are fully cutting though anvil 60 and are longitudinal open channels starting on tissue facing surface 160 and terminating on anvil 60 side opposing tissue facing side 160, with central flaps 105a partially exposed on side of anvil 60 opposite tissue facing side of anvil 60. Not shown are alternative embodiments similar to embodiments of FIG. 39 whereby buttress 100a is pre-cut into two halves positioned on both sides of channel 62.

In operation, embodiments with central flaps 105, 105A of FIGS. 36C, 36D, and 37-41 operate in a similar fashion to the embodiments with peripheral flaps 110, 110a, whereby upon deployment of staples and resecting of tissue T or tissue layers T1 and T2, buttress 100, 110a is stapled to the tissue and is cut into two halves by the action of knife member. Buttress 100, 100a remains attached to stapled and resected tissue and is separated from cartridge 70 or anvil 60, with central flaps 105 and/or 105a moving from storage position within grooves 172, 172a. Central flaps 105 and/or 105a are then unfurled from the folded storage position and wrapped around the resected tissue edge. The difference with the embodiments where peripheral flaps 110 or 110a are positioned on the periphery of buttress 100 or 100a is that central flaps 105 and 105a do not need to be flipped over or folded back, but can be directly wrapped around tissue edge 120.

Figure 42:
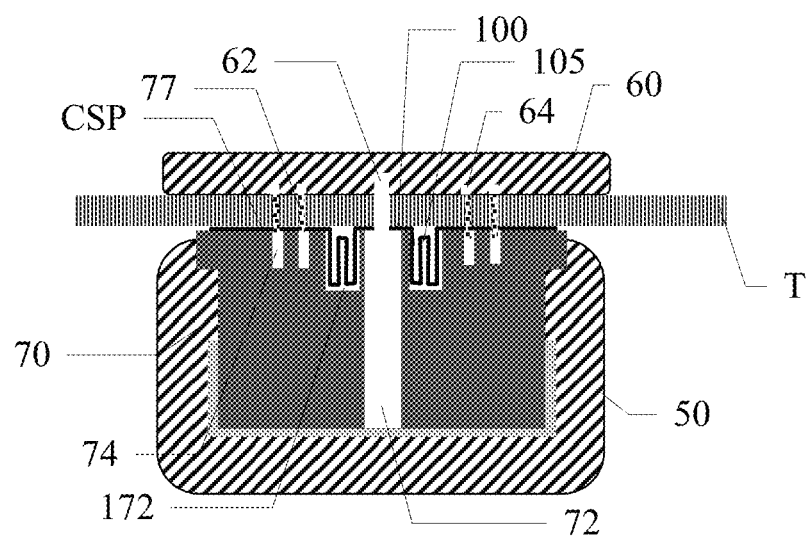
FIG. 42 shows a simplified cross-sectional view of tissue positioned between anvil and cartridge installed in the end effector, after resection and stapling, with a buttress having central flaps.

Referring now to FIG. 42, a simplified cross-sectional view is presented of the position after deployment of staples 77 and resecting tissue T. One layer of tissue T as shown, but several layers, such as tissues T1 and T2 as presented above can be stapled. Buttress 100 is shown stapled to tissue T by staples 77 and cut into two halves by the action of knife member 80 (not shown in FIG. 42) as knife member 80 resects/cuts tissue.

Referring to FIG. 43A, a simplified cross-sectional view is presented of the position after opening of stapler 10 i.e. separation of lower jaw 50 and anvil 60 after stapling and removal of stapler 10. Buttress 100 remains attached to stapled and resected tissue T by staples 77. Buttress 100 with central flap 105 has separated from cartridge 70, with central flap 105 moving from its storage position within groove 172. Only one side of resected tissue T is shown for simplification. Tissue T has formed an exposed resection edge 120.

Central flap 105 is then unfurled from its folded storage position and wrapped around the resected edge 120, as schematically indicated by arrow in FIG. 43B, resulting in the position of the central flap 105 shown in FIG. 43C. As can be seen, central flap 105 is covering tissue edge 120 and at least a portion of tissue surface S1 which is opposite to tissue surface S2. Peripheral Stapled Portion PSP of buttress 100 is stapled to tissue surface S2, and central flap 105 wraps around tissue T starting at surface S2, goes over tissue edge 120, and covers at least a portion of tissue surface S1, which will help hemostasis and tissue sealing, improve healing, prevent adhesions.

The above operating description is also applicable to other embodiments of the present invention employing central flaps 105, 105a for anvil 60 mounted buttress 100a, buttress 100a is stapled to tissues T1 and T2 or single layer tissue T and is cut into two halves by the action of knife member 80 as knife member 80 resects/cuts tissue. After stapling and removal of stapler 10, buttress 100a remains attached to stapled and resected tissues T1 and T2, with central flaps 105a separating from anvil 60. Central flap 105a is then unfurled from its folded storage position and wrapped around the resected edge 120.

Differently from embodiments having peripheral flaps 110, 110a, central flaps 105, 105a are contacting tissue edge 120 and opposing tissue side S1 with the same side of buttress 100 that is in contact with tissue T, in other words with the side of buttress 100 that is in contact with tissue T surface S2.

Similarly to the embodiments with peripheral flaps 110, 110a, embodiments with central flaps 105, 105a may have optional fixating means are provided for fixating on edge 120, and/or, on tissue surface S1. In some embodiments, there is provided an adhesive coating or adhesive layer on buttress side facing towards tissue T surface S2, with at least adhesive layer disposed on central flap 105, 105a.

As central flaps 105, 105a are wrapped about resected tissue edge 120 and brought into contact with tissue surface S1, flaps can be secured to tissue edge 120 and/or to surface S1 by the action of the adhesive, miniature anchors such as barbed pins, moisture activated composition having high adherence to wet tissues, and the like.

The width of peripheral stapled portion PSP of buttress 100 comprises two peripheral portions of buttress 100, 100a separated by two central flaps 105, 105a. The width of PSP is configured to ensure there is a portion of buttress 100, 100a covering stapled area or covering stapling lines 740 or covering staple pockets 74 or staple forming pockets 64.

In some embodiments, the width of peripheral stapled portion PSP of buttress 100 comprises is from about one half of tissue facing surface 170 or 160 width to about 0.9 times tissue facing surface 170 or 160 width, such as 0.6; 0.7; 0.8 times tissue facing surface width.

The width of central flaps 105, 105a is configured so that central flaps can be wrapped around resected tissue edge 120. In some embodiments, the width of each central flap 105, 105a is at least equal to or larger than the thickness of tissue T or combined thicknesses of tissues T1 and T2, such as 1, 1.25, 1.5, 1.75, 2, 2.5, 3, 4.5, 4, 4.5, 5, 8, 10, 15 times the thickness of tissue, most preferably 2-5 times thickness of tissue.

Similarly to the embodiments with peripheral flaps 110, 110a, embodiments with central flaps 105, 105a may have buttress 100, 100a comprising single layer of uniform thickness material or a multilayer material or single layer material of non-uniform thickness.

Figure 44A:
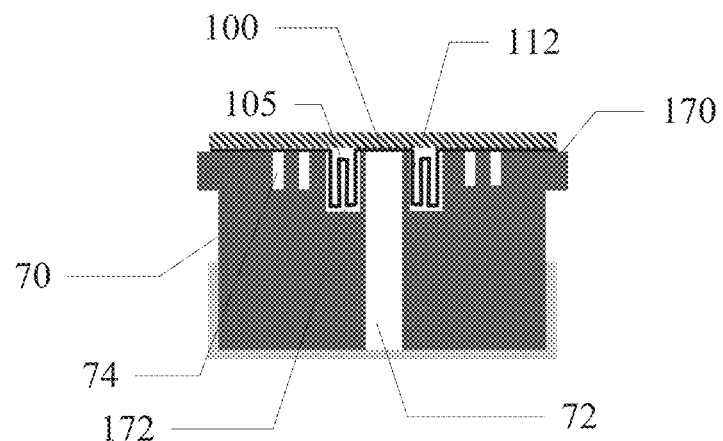
FIGS. 44A-C show simplified cross-sectional views of cartridge with two-layer buttress disposed on tissue facing surface with flaps folded.

Referring to FIG. 44A, showing a schematic cross-sectional view of cartridge 70 with buttress 100 having central flaps 105, an additional layer 112 is disposed on top of buttress 100, distal to surface 170, wherein layer 112 can be optionally less flexible and/or thicker than material of central flap 105. Layer 112 can be configured for tissue support and/or staple line reinforcement, and is configured to remain opposite tissue T surface S2. Layer 112 can be integrated into buttress 100.

Figure 44B:
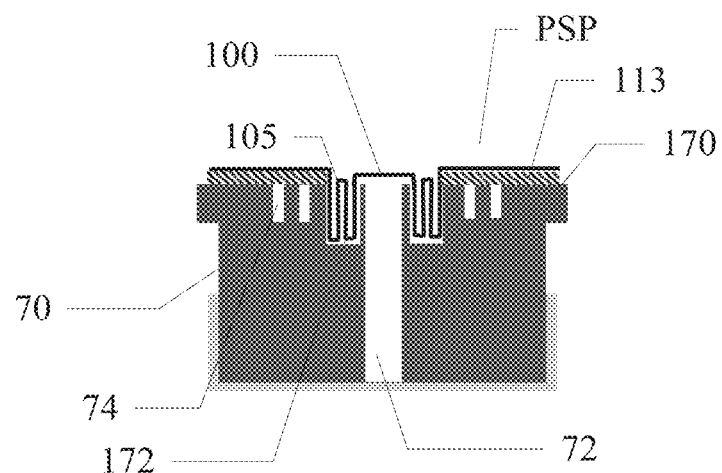

Referring to FIG. 44B, showing a schematic cross-sectional view of cartridge 70 with buttress 100 having central flaps 105, an additional layer 113 is disposed between buttress 100 and surface 170 of cartridge 70. Layer 113 can be optionally less flexible and/or thicker than material of central flap 105. Layer 113 can be configured for tissue support and/or staple line reinforcement and can be integrated into buttress 100.

Figure 44C:
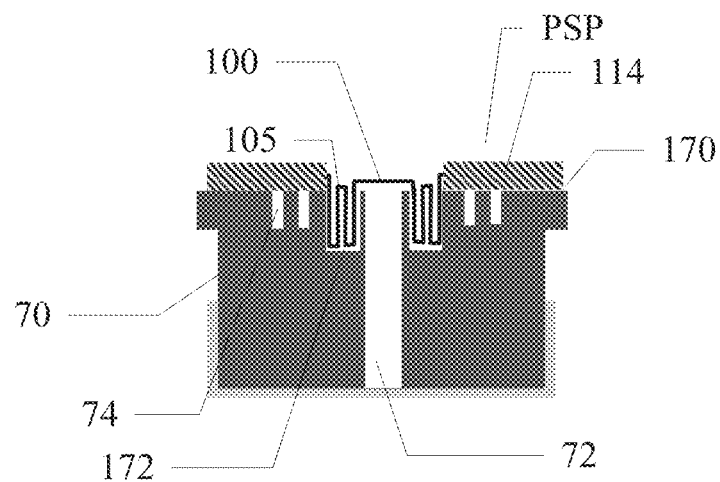

Referring to FIG. 44C, showing a schematic cross-sectional view of cartridge 70 with buttress 100 having central flaps 105, buttress 100 is shown having thicker peripheral stapled portions 114, or PSP, and thinner central flaps 105. Portions 114 can be optionally less flexible and/or thicker than material of central flap 105. Portions 114 can be configured for tissue support and/or staple line reinforcement and are integrated into buttress 100.

Layers 112, 113, 114 can be made of the same material as buttress 100, or of a different material.

In operation, only flexible central flap is unfurled from stored position and wrapped over resected edge 120 after stapling/resection; layers 112, 113, 114 are used to reinforce stapled tissue and are not folded or wrapped over tissue edge 120.

The width of layers 112, 113, 114 can be substantially equivalent to width of cartridge 70. Alternatively, the width of layers 112, 113, 114 is at least wide enough to cover the stapled area i.e. area between outermost rows of staple pockets 74.

In one embodiment, buttress 100 is deployed on cartridge 70, and buttress 100a is deployed on anvil 60, with peripheral flaps 110 and 110a and/or central flaps 105 and 105a wrapped over/folded over the resected edge (from one surface of tissue and another from opposing surface of tissue in overlapping configuration, and secured to each other by Velcro-like entanglement, adhesive or any other securement mechanism.

In one embodiment, buttress 100 or 100a comprises both central flaps 105, 105a and peripheral flaps 110, 110a. After stapling and resection, peripheral flaps 110 or 110a and central flaps 105 or 105a wrapped over/folded over the resected edge from the same surface of tissue and in overlapping configuration.

In certain embodiments, peripheral flaps 110 and 110a and/or central flaps 105 and 105a are shape memory material, which upon exposure to moisture unfurls to cover edge 120 and opposing tissue surface. The mechanisms of unfurling are for instance a bi-layer flap (not shown) with a high shrinkage coefficient upon exposure to moisture of layer of flap facing opposite of tissue T2 and/or high expansion coefficient upon exposure to moisture of layer of peripheral flap 110 facing tissue T2. Shrinkage and/or expansion upon absorbing moisture will result in automatic unfurling of flaps and wrapping of flaps over edge 120 and opposing tissue T1.

Buttress 100, 100a and/or flaps 110, 110a, 105, 105a can optionally be coated with or impregnated with biomedically useful agents, such as agents promoting healing and preventing inflammation and infections. The biomedically useful agents are then into the surrounds over time, such time ranging from a few hours to several days to several weeks, such as 12 hours, 24 hours, 48 hours, 1 week, 2 weeks, 4 weeks, 12 weeks, with such medicant release referred to as sustained release of biomedically useful agents.

Biomedically useful agents or therapeutic material refers to any medically useful substance or combination of substances, which can improve tissue viability, including drugs, enzymes, growth factors, peptides, proteins, nutrients, excipients, antimicrobial agents, and any other injectable pharmaceutical agents. Of particular interest are hemostatic agents such as thrombin and or fibrinogen. Other examples of therapeutic agents are autologous cells.

Buttress 100, 100*a* and/or flaps 110, 110*a*, 105, 105*a* are preferably made of any suitable biocompatible material or composite in a form of non-woven, felt, knit, woven, molded sheet, and the like. Buttress 100, 100*a* and/or flaps 110, 110*a*, 105, 105*a* of the present invention may be fabricated from any biodegradable and/or nonbiodegradable material, including polymers, that can be used in surgical procedures. The term "biodegradable" is defined to include both bioabsorbable and bioresorbable materials. Materials include natural, synthetic, bioabsorbable, and/or nonabsorbable materials, and combinations thereof. Natural biodegradable polymers which may be used to form Buttress 100, 100*a* and/or flaps 110, 110*a*, 105, 105*a* include native materials or derivatives of: polysaccharides such as chitosan, cellulose, collagen, gelatin, alone or in combination with biologic materials and/or synthetic polymers. Examples of cellulose derivatives include carboxymethyl cellulose, oxidized cellulose, oxidized regenerated cellulose, and the like, and combinations thereof. Synthetic biodegradable polymers which may be utilized to form medical devices include various known bioerodible/bioresorbable polymers, such as poly(lactide co-glycolide) and more generally polymers and co-polymers made from glycolide, lactide, ε-caprolactone, trimethylene carbonate, p-dioxanone, and the like, and combinations thereof. Non-degradable materials can include polyethylene, polypropylene, polytetrafluoroethylene; nylon, and similar.

The thickness of buttress 100 is from about 0.05 mm to about 3 mm, more preferably from 0.1 mm to 2 mm, such as 0.2, 0.5, 0.8, 1.0, 1.5 mm.

The width of buttress 100 including flaps is at least 1.3 the width of tissue facing surface 170 of cartridge 70, more preferably at least 1.5; 2; 3 times the width of tissue facing surface 170 of cartridge 70. In some embodiments the width of buttress 100 including flaps 110 is from 15 mm to 60 mm, such as 20, 25, 30, 35, 40 mm.

In some embodiments each flap has a width that is equal to or larger than the 0.5 times the width of tissue facing surface 160, 170, such as 0.75, 1, 1.5, 2 times the width of tissue facing surface 160, 170.

In some embodiments each flap has a width that is larger than the sum of the distance between channel 72 and farthest row of staple pockets 74 and the thickness of tissues T1 and T2 being stapled, such as larger by 5 mm, 10 mm, 15 mm, 20 mm, 30 mm.

The length of buttress 100, 100*a* is from about 0.5 to about 1.3 times the length of tissue facing surface 170 or 160, such as 0.75; 1.0; 1.2 times the length of tissue facing surface 170 or 160. In some embodiments, the length of buttress 100, 100*a* is equal or 5-20% larger than the length of stapled area or length of staples lines 740.

The above description is applicable to joining and resecting two or more layers of tissue T1 and T2 or single layer of tissue T. However, the same operating and structural approach is applicable to joining more than two tissue layers, or to resecting and closing one tissue layer, such as for instance pleura or lung tissue, liver tissue, kidney tissue, etc. As was disclosed with reference to FIGS. 26B, 42, 43, only one tissue layer, designated as T and having surfaces S1 and S2, can be resected and stapled, with surface S2 corresponding to tissue T2 of and surface S1 corresponding to tissue T1 of FIGS. 23-28, 30.

Figure 45:
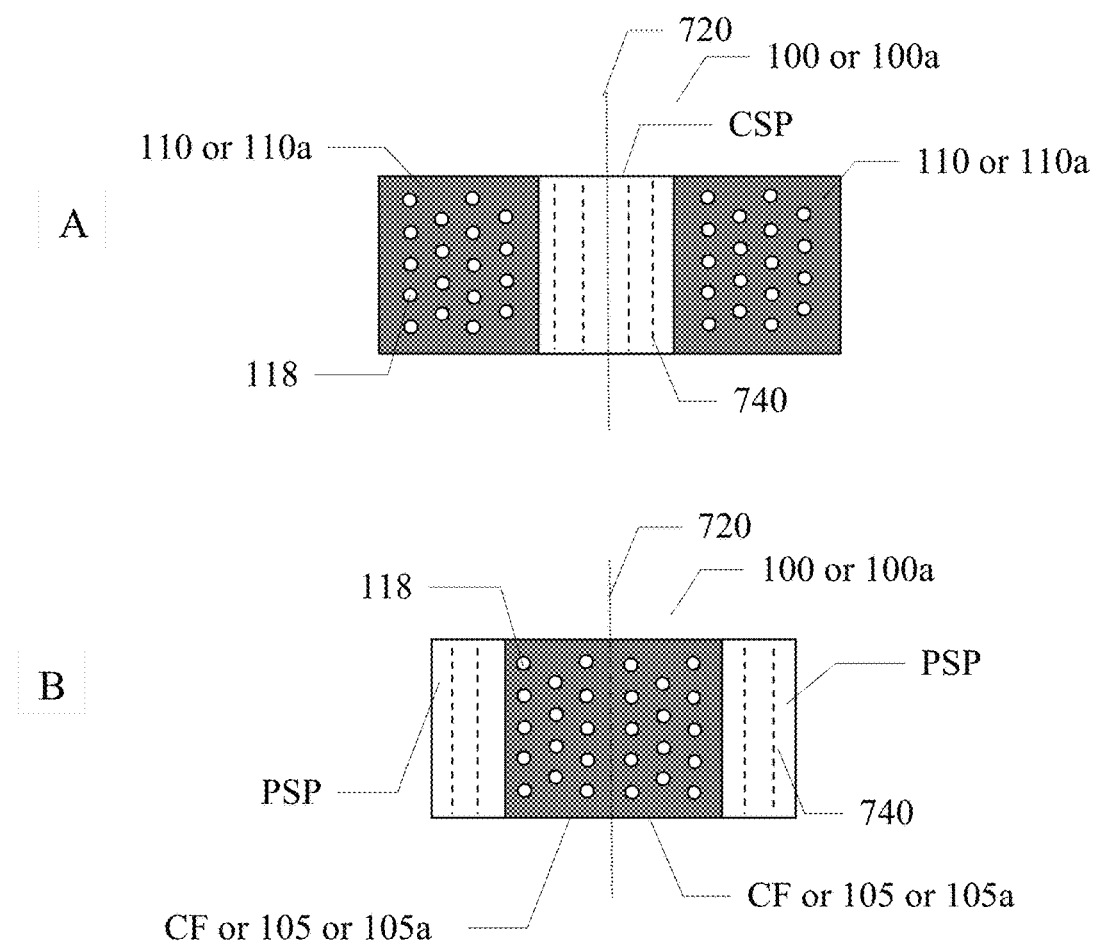
FIGS. 45A and 45B show schematic top views of buttress with peripheral flaps and buttress with central flaps, with flaps having pores or apertures and shown in flat planar view.

Referring now to FIG. 45, in some embodiments flap portions have a plurality of pores or apertures 118. Advantageously, pores or apertures can provide for better tissue healing.

As shown in FIG. 45A, peripheral flaps 110 or 110*a* have apertures 118 or pores 118. As shown in FIG. 45B, central flaps 105 or 105*a* have apertures 118.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

What is claimed is:

1. A surgical stapler for stapling and resecting at least one section tissue comprising:
a body, a shaft assembly, and an end effector, wherein the end effector comprises a lower jaw configured to receive a staple cartridge, an anvil pivotable toward and away from the lower jaw, and a translatable knife member; a disposable cartridge installed in the lower jaw, said cartridge containing a plurality of deployable staples in arrays separated by a tissue resection channel through which the knife member can translate;
said anvil having a plurality of staple forming pockets aligned with said deployable staples; a surgical buttress at least partially disposed on a tissue facing surface of at least one of the cartridge or the anvil, said buttress having width larger than width of said tissue facing surfaces; said buttress comprising a first portion positioned over the deployable staples or over the staple forming pockets, and at least one flap portion not positioned over the deployable staples or over the staple forming pockets;
said flap portion folded or rolled on itself and unfurlable and wrappable about the resected tissue.

2. The surgical stapler of claim 1, wherein said buttress comprises two flap portions.

3. The surgical stapler of claim 2, wherein said flap portions are configured to wrap around the resected tissue.

4. The surgical stapler of claim 3, wherein said flap portions are stored folded on said tissue facing surface of at least one of the cartridge or the anvil.

5. The surgical stapler of claim 3, wherein said flap portions are stored rolled up outside of said tissue facing surface of at least one of the cartridge or the anvil.

6. The surgical stapler of claim 3, wherein said buttress comprises at least two layers.

7. The surgical stapler of claim 3, wherein said flap portions are located on a periphery of said buttress and are surrounding said first portion, said flap portions each having a width larger than one half of the width of said tissue facing surface.

8. The surgical stapler of claim 7, wherein said flap portions each having the width larger than the width of said tissue facing surface.

9. The surgical stapler of claim 3, wherein said flap portions are located in a center of said buttress and said first portion comprises two parts surrounding said flap portions, said flap portions each having a width larger than thickness of the tissue or larger than one half of the width of said tissue facing surface.

10. A method of using the surgical stapler of claim 3, comprising the steps of:

inserting the staple cartridge into the lower jaw;

capturing tissue between the anvil and the staple cartridge;

translating the knife member distally from a proximal position to a distal position simultaneously cutting the captured tissue forming a resected tissue edge and driving the plurality of staples of the staple cartridge through the captured tissue, simultaneously attaching said first portion of said buttress to a first tissue surface with staples and cutting said buttress in two halves while not attaching said flap portions to said tissue with said staples;

removing said surgical stapler from contact with tissue leaving said buttress attached to the first tissue surface;

unfurling at least one of said flap portions and wrapping said at least one flap portion around the resected tissue edge and optionally bringing said at least one flap portion in contact with a second tissue surface opposing the first tissue surface.

11. The method of claim 10, wherein the step of unfurling at least one of said flap portions and wrapping said at least one flap portion around the resected tissue edge further comprises folding the flap portion backward on itself.

12. The method of claim 10, further comprising a preparation step comprising attaching said buttress to said anvil, said cartridge, or to both said anvil and said cartridge.

13. The surgical stapler of claim 2, wherein said buttress is rectangular.

14. The surgical stapler of claim 2, wherein said flap portions are porated.

15. The surgical stapler of claim 2, wherein said buttress is at least partially bioresorbable or at least partially soluble.

16. The surgical stapler of claim 2, wherein said buttress comprises a releasable medically useful agent.

17. The surgical stapler of claim 1, wherein said first portion comprises two layers, and said flap portion comprises one layer.

18. The surgical stapler of claim 1, wherein said first portion has higher thickness, and said flap portion has lower thickness.

19. The surgical stapler of claim 1, wherein said flap portion comprises a layer of adhesive or at least one barbed pin.

* * * * *